US012797544B2

(12) United States Patent
Abraham et al.

(10) Patent No.: US 12,797,544 B2
(45) Date of Patent: Nov. 17, 2026

(54) SYSTEMS, DEVICES AND METHODS FOR INTRADERMAL OR SUBDERMAL FLUID DELIVERY

(71) Applicant: ACOM Labs, Inc., San Francisco, CA (US)

(72) Inventors: Jack Phillip Abraham, Miami Beach, FL (US); Callie Mackenzie Roberts, Martinez, CA (US); Liang Liu, Leander, TX (US); Dehui Kong, Newark, CA (US); Healey Thomas Cypher, San Francisco, CA (US); Paul F. Bente, IV, Westford, MA (US); Stefanie Alyse Hurowitz, Conshohocken, PA (US); Nicholas Frank Bruno, Pottstown, PA (US); Andrew Nathan King, King of Prussia, PA (US); Nicholas Joseph Ciccarelli, Glen Mills, PA (US)

(73) Assignee: ACOM Labs, Inc., San Francisco, CA (US)

( * ) Notice: Subject to any disclaimer, the term of this patent is extended or adjusted under 35 U.S.C. 154(b) by 263 days.

(21) Appl. No.: 18/579,762

(22) PCT Filed: Jul. 20, 2022

(86) PCT No.: PCT/US2022/073953

§ 371 (c)(1),
(2) Date: Jan. 16, 2024

(87) PCT Pub. No.: WO2023/004355

PCT Pub. Date: Jan. 26, 2023

(65) Prior Publication Data

US 2024/0293652 A1 Sep. 5, 2024

Related U.S. Application Data

(60) Provisional application No. 63/235,085, filed on Aug. 19, 2021, provisional application No. 63/223,915, filed on Jul. 20, 2021.

(51) Int. Cl.
*A61M 5/20* (2006.01)
*A61M 5/46* (2006.01)
*A61M 37/00* (2006.01)

(52) U.S. Cl.
CPC ............ *A61M 5/20* (2013.01); *A61M 5/2033* (2013.01); *A61M 5/46* (2013.01);
(Continued)

(58) Field of Classification Search
CPC ........ A61M 5/20; A61M 5/2033; A61M 5/46; A61M 2005/206
See application file for complete search history.

(56) References Cited

U.S. PATENT DOCUMENTS

| | | | | |
|---|---|---|---|---|
| 5,034,002 | A | 7/1991 | Duranzampa et al. | |
| 5,695,472 | A * | 12/1997 | Wyrick ............ | A61M 5/31595 604/211 |

(Continued)

FOREIGN PATENT DOCUMENTS

| | | | |
|---|---|---|---|
| BR | 1120240012131 | A2 | 4/2024 |
| BR | 1120240056937 | A2 | 7/2024 |

(Continued)

OTHER PUBLICATIONS

International Search Report and Written Opinion received for International Application No. PCT/US2022/073953, Search completed Nov. 2, 2022, Mailed Nov. 23, 2022, 14 pgs.

(Continued)

*Primary Examiner* — William H Rodriguez
(74) *Attorney, Agent, or Firm* — KPPB LLP

(57) ABSTRACT

Systems, devices, and methods for intradermal or subdermal fluid delivery via a microneedle are provided. A delivery system can include an injector, fluid-filled cartridge or syringe, and a needle. A cartridge or syringe can be compatibly coupled with an injector device such that the injector
(Continued)

device is capable of ejecting fluid out of the cartridge and though the needle. Fluid delivery systems can be utilized in a number of applications, including medications and supplements for the skin.

33 Claims, 26 Drawing Sheets

(52) U.S. Cl.
CPC ... *A61M 2005/206* (2013.01); *A61M 37/0015* (2013.01); *A61M 2037/0023* (2013.01); *A61M 2037/0061* (2013.01)

(56) References Cited

U.S. PATENT DOCUMENTS

| | | | | |
|---|---|---|---|---|
| 7,563,252 | B2 | 7/2009 | Marshall et al. | |
| 8,591,463 | B1 * | 11/2013 | Cowe | A61M 5/20 604/117 |
| 9,707,344 | B2 * | 7/2017 | Cowe | A61M 5/2033 |
| 12,383,683 | B1 * | 8/2025 | Denyer | A61M 5/31526 |
| 12,434,008 | B1 * | 10/2025 | Hee-Hanson | A61M 5/31565 |
| 2008/0097312 | A1 * | 4/2008 | Wilmot | A61M 5/46 604/117 |
| 2010/0094214 | A1 | 4/2010 | Abry et al. | |
| 2010/0160857 | A1 | 6/2010 | Pongpairochana et al. | |
| 2013/0053790 | A1 * | 2/2013 | Karlsson | A61M 5/2033 604/218 |
| 2013/0218093 | A1 * | 8/2013 | Markussen | A61M 5/001 604/198 |
| 2013/0274676 | A1 * | 10/2013 | Ekman | A61M 5/31513 604/197 |
| 2014/0012229 | A1 * | 1/2014 | Bokelman | A61M 5/31513 604/154 |
| 2014/0257191 | A1 | 9/2014 | Cowe | |
| 2015/0246181 | A1 | 9/2015 | Fourt et al. | |
| 2017/0367729 | A1 | 12/2017 | Ginggen et al. | |
| 2018/0015232 | A1 | 1/2018 | Iwase | |
| 2018/0140774 | A1 * | 5/2018 | Constantineau | A61M 5/31596 |
| 2018/0296761 | A1 | 10/2018 | Cowe et al. | |
| 2019/0365998 | A1 | 12/2019 | Henderson et al. | |
| 2020/0197611 | A1 * | 6/2020 | O'Connor | A61M 5/3148 |
| 2020/0360621 | A1 * | 11/2020 | Franke | A61M 5/326 |
| 2020/0397999 | A1 * | 12/2020 | Franke | A61M 5/2033 |
| 2021/0038829 | A1 * | 2/2021 | Montgomery | A61M 5/3204 |
| 2021/0146057 | A1 | 5/2021 | King et al. | |
| 2021/0260295 | A1 * | 8/2021 | Soares | A61M 5/326 |
| 2022/0134019 | A1 | 5/2022 | Besson et al. | |
| 2024/0033430 | A1 * | 2/2024 | Boström | A61M 5/20 |
| 2024/0123150 | A1 * | 4/2024 | Urbanek | A61M 5/3157 |
| 2024/0407718 | A1 * | 12/2024 | Abraham | A61M 5/427 |
| 2025/0050033 | A1 * | 2/2025 | Miley | A61M 5/2033 |
| 2025/0065054 | A1 * | 2/2025 | Carlsson | A61M 5/3158 |
| 2025/0144298 | A1 * | 5/2025 | McCawley | A61M 5/2033 |
| 2025/0339620 | A1 * | 11/2025 | Mikkelsen | A61M 5/2033 |
| 2026/0151571 | A1 * | 6/2026 | Wiklund | A61M 5/2033 |

FOREIGN PATENT DOCUMENTS

| | | | |
|---|---|---|---|
| CN | 117915971 | A | 4/2024 |
| CN | 118234427 | A | 6/2024 |
| EP | 2468334 | A1 | 6/2012 |
| EP | 4373550 | A1 | 5/2024 |
| EP | 4404829 | A1 | 7/2024 |
| IN | 202417011357 | A | 3/2024 |
| IN | 202417031798 | A | 11/2024 |
| JP | 2008536599 | A | 9/2008 |
| JP | 2008543500 | A | 12/2008 |
| JP | 2017525466 | A | 9/2017 |
| JP | 2024525912 | A | 7/2024 |
| JP | 2024536060 | A | 10/2024 |
| KR | 102059772 | B1 | 12/2019 |
| KR | 20240036627 | A | 3/2024 |
| KR | 20240065162 | A | 5/2024 |
| MX | 2024000942 | A | 4/2024 |
| MX | 2024003571 | A | 5/2024 |
| WO | 2005113039 | A1 | 12/2005 |
| WO | 2016036600 | A1 | 3/2016 |
| WO | 2019234177 | A1 | 12/2019 |
| WO | 2023004355 | A1 | 1/2023 |
| WO | 2023049907 | A1 | 3/2023 |

OTHER PUBLICATIONS

International Search Report and Written Opinion received for International Application No. PCT/US2022/077038, Search completed Dec. 18, 2022, Mailed Feb. 6, 2023, 24 pgs.

International Preliminary Report on Patentability received for International Application No. PCT/US2022/073953, Report issued Jan. 18, 2024, Mailed Feb. 1, 2024, 08 pgs.

International Preliminary Report on Patentability received for International Application No. PCT/US2022/077038, Report issued Mar. 26, 2024, Mailed Apr. 4, 2024, 8 pgs.

Extended European Search Report received for European Application No. 22846818.7, Search completed Mar. 27, 2025, Mailed Apr. 10, 2025, 13 pgs.

Extended European Search Report received for European Application No. 22873923.1, Search completed Jul. 8, 2025, Mailed Jul. 17, 2025, 10 pgs.

Baran et al., "High Resolution Imaging of Acne Lesion Development and Scarring in Human Facial Skin Using OCT-Based Microangiography", Lasers in Surgery and Medicine, vol. 47, No. 3, Mar. 2015, pp. 231-238, doi: 10.1002/lsm.22339.

Chan et al., "Machine Learning in Dermatology: Current Applications, Opportunities, and Limitations", Dermatology and Therapy, vol. 10, No. 3, Jun. 2020, pp. 365-386, doi: 10.1007/s13555-020-00372-0.

Cullell-Dalmau et al., "Convolutional Neural Network for Skin Lesion Classification: Understanding the Fundamentals Through Hands-on Learning", Frontiers in Medicine, vol. 8, Article 644327, Mar. 4, 2021, 8 pgs., doi: 10.3389/fmed.2021.644327.

Gomolin et al., "Artificial Intelligence Applications in Dermatology: Where Do We Stand?", Frontiers in Medicine, vol. 7, Article 100, Mar. 31, 2020, 7 pgs., doi: 10.3389/fmed.2020.00100.

Halani et al., "Ultrasound and Infrared-Based Imaging Modalities for Diagnosis and Management of Cutaneous Diseases", Frontiers in Medicine, vol. 5, Article 115, Apr. 25, 2018, 15 pgs., doi: 10.3389/fmed.2018.00115.

Humayun et al., "Multispectral and Thermal Images for Acne Vulgaris Classification", National Postgraduate Conference, Sep. 2011, 4 pgs., doi: 10.1109/NatPC.2011.6136336.

Kollias et al., "Optical Non-Invasive Approaches to Diagnosis of Skin Diseases", Journal of Investigative Dermatology Symposium Proceedings, vol. 7, No. 1, Dec. 2002, pp. 64-75, doi: 10.1046/j.1523-1747.2002.19635.x.

Levine et al., "Introduction to reflectance confocal microscopy and its use in clinical practice", JAAD Case Reports, Confocal Microscopy, vol. 4, No. 10, Nov. 10, 2018, pp. 1014-1023, doi: 10.1016/j.jdcr.2018.09.019.

Liu et al., "SSD: Single Shot MultiBox Detector", arXiv:1512.02325 [cs.CV], Dec. 29, 2016, 17 pgs.

Manfredini et al., "In vivo monitoring of topical therapy for acne with reflectance confocal microscopy", Skin Research and Technology, vol. 23, No. 1, Feb. 2017, pp. 36-40, doi: 10.1111/srt.12298.

Upadhyay et al., "An improved bag of dense features for skin lesion recognition", Journal of King Saud University: Computer and Information Sciences, vol. 34, No. 3, Mar. 2022, pp. 520-525, doi: 10.1016/j.jksuci.2019.02.007.

Weinhold et al., "Improving the safety of disposable auto-injection devices: a systematic review of use errors", AAPS Open, vol. 4, Article 7, Oct. 2018, 14 pgs., doi: 10.1186/s41120-018-0027-z.

* cited by examiner

SYSTEMS, DEVICES AND METHODS FOR INTRADERMAL OR SUBDERMAL FLUID DELIVERY

CROSS REFERENCE TO RELATED APPLICATIONS

This application is a national stage of PCT Patent Application No. PCT/US2022/073953 entitled "Systems, Devices and Methods for Intradermal or Subdermal Fluid Delivery" filed Jul. 20, 2022, which claims priority to U.S. Provisional Application Ser. No. 63/223,915, entitled "Systems, Devices and Methods for Intradermal or Subdermal Fluid Delivery," filed Jul. 20, 2021, and U.S. Provisional Application Ser. No. 63/235,085, entitled "Systems, Devices and Methods for Dermal Treatments," filed Aug. 19, 2021, the disclosures of which are each incorporated herein by reference in its entirety.

TECHNICAL FIELD

The application is generally directed to systems, devices, and methods for intradermal or subdermal fluid delivery, and more specifically to systems, devices, and methods that utilize controlled injection amount and depth for delivery of medicinal or supplemental fluid into or just below the dermis.

BACKGROUND

Hollowed microneedles are small applicators to deliver fluids, especially vaccines or medications. Microneedles are typically used in transdermal, intraocular, or intracochlear fluidic delivery. Because of their small size, microneedles typically do not cause injury to the site of injection and are generally considered less hazardous than other injection methods, such as a conventional hypodermic needle.

SUMMARY

The disclosure generally provides systems, devices, and methods for intradermal or subdermal fluid delivery. In various implementations, the various systems, the various devices, or the various methods control the amount of fluid to be delivered. In various implementations, the various systems, the various devices, or the various methods control the depth of needle insertion at site of injection, especially within the intradermal layer. In various implementations, the various systems, the various devices, or the various methods conceal and/or cover the needle from a user, which can prevent harm to the user and/or prevent damage to the needle.

In an aspect, a system for intradermal or subdermal fluid delivery into a site injection comprises a housing compartment. The housing compartment comprises a flange holder system, a plunger retainer system, and an actuator of an injection mechanism that expels a controlled dose fluid.

In some implementations, the flange holder system comprises a movable flange holder and a flange holder hard stop.

In some implementations, the plunger retainer system comprises a moveable plunger retainer and a plunger retainer hard stop.

In some implementations, the flange holder and the plunger retainer are each movable in an proximal direction along a central axis of the housing compartment.

In some implementations, actuation of the injection mechanism via the actuator results in the flange holder and the plunger retainer moving in the proximal direction until the flange holder contacts the flange holder hard stop halting the proximal movement of the flange holder.

In some implementations, the flange holder contacts the flange holder hard stop, the plunger retainer continues to move in the proximal direction until the plunger retainer contacts the plunger retainer hard stop halting the proximal movement of the plunger retainer.

In some implementations, the system for intradermal or subdermal fluid delivery into a site injection further comprises a fluid-filled syringe comprising a flange and a plunger.

In some implementations, the flange is situated within the flange holder and plunger is situated in the plunger retainer of the housing compartment.

In some implementations, the system for intradermal or subdermal fluid delivery into a site injection further comprises a needle assembly attached to the fluid-filled syringe. The needle assembly comprises a needle that is in operable connection with the fluid-filled syringe.

In some implementations, actuation of the injection mechanism via the actuator results in the flange holder and the plunger retainer moving in the proximal direction resulting in moving the fluid-filled syringe inclusive of the flange and the plunger, and the needle assembly in the proximal direction until the flange holder contacts the flange holder hard stop halting the proximal movement of the flange and the needle assembly. When the flange holder contacts the flange holder hard stop, the plunger retainer continues to move in the proximal direction resulting in the plunger to continue to move in the proximal direction until the plunger retainer contacts the plunger retainer hard stop halting the proximal movement of the plunger. The continued proximal movement of the plunger after the halting of the proximal movement of the flange and the needle assembly results in the expulsion of the controlled dose of fluid from the fluid-filled syringe via the needle of the needle assembly.

In some implementations, the flange holder comprises a groove, and the plunger retainer comprises a slider that cooperates within the groove. When the flange holder contacts the flange holder hard stop, the plunger retainer continues to move in the proximal direction via the slider within the groove.

In some implementations, a latch connects the flange holder and the plunger retainer. When the flange holder contacts the flange holder hard stop, the latch is released allowing the plunger retainer to continue to move in the proximal direction independent of the flange holder movement.

In some implementations, the system for intradermal or subdermal fluid delivery into a site injection further comprises a force for providing proximal movement. The plunger retainer is in connection with the force for providing proximal movement such that the plunger retainer moves in the proximal direction via the actuation of the injection mechanism. The flange holder moves in the proximal direction via the latch connecting the flange holder and the plunger retainer.

In some implementations, the force for providing proximal movement is a compressed spring.

In some implementations, the force for providing proximal movement is an electromechanical linear actuator.

In some implementations, the dose amount of the controlled dose of fluid is determined in part by the continued proximal movement of the plunger after the halting of the proximal movement of the flange and the needle assembly.

In some implementations, the movement of the flange holder in the proximal direction is configured to result in the needle inserting into a site of injection when a proximal face of the housing compartment is in contact with the site of injection.

In some implementations, the syringe flange holder contains an indentation that is contoured to the shape of the flange.

In some implementations, the plunger retainer holder contains at least one indentation that is contoured to the shape of a plunger grip at the distal end of the plunger.

In some implementations, the plunger retainer holder contains a plurality of indentations that allow for flexibility of the plunger grip location.

In some implementations, the actuator of the injection mechanism comprises a button.

In some implementations, one or more inward protruding struts is in connection with button and the flange holder. When the button is depressed, the one or more inward protruding struts prevents proximal movement of the flange holder. Compression of the button results in a disconnection between the one or more inward protruding struts and the flange holder, allowing proximal movement of the flange holder.

In some implementations, compression of the button results in linear force provided by an electromechanical linear actuator to provide proximal movement of the plunger retainer.

In some implementations, the needle has a length that such that the needle tip extends beyond the proximal face a length equal to an intradermal insertion depth when inserted into skin of an individual.

In some implementations, the needle assembly further comprises a needle cap. The needle has a length such that the needle tip extends beyond the needle cap a length equal to an intradermal insertion depth when inserted into skin of an individual.

In some implementations, the needle assembly further comprises a needle cover that surrounds the needle and a spring in connection with the needle cover. When the spring is decompressed, the needle cover prevents exposure of a tip of the needle. When the spring is compressed, the tip of the needle is exposed.

In some implementations, the needle assembly further comprises an outer cylinder encircling the needle cover. An inner face of the outer cylinder comprises one or more slotted tracks. The needle cover comprises a protruding slider that extends from an outer face of the needle cover and into the one or more slotted tracks. The interaction between the protruding slider and the one or more slotted tracks allows for limited exposure of the needle when the spring is compressed.

In some implementations, the limited exposure of the needle allows for positioning of the needle tip beyond the needle cover.

In some implementations, the positioning of the needle tip beyond the needle cover results in an intradermal insertion depth when inserted into skin of an individual.

In some implementations, the needle assembly further comprises an actuator with an arm that is capable of inserting within the one or more slotted tracks. The needle assembly actuator with the arm is capable of preventing exposure of the needle by preventing compression of the spring by preventing the protruding slider from moving within the one or more slotted tracks.

In some implementations, opening of the needle assembly actuator with the arm allows exposure of the needle. The opening of the needle assembly actuator opens up at least one slotted track of the one or more slotted tracks to allow movement of the protruding slider and compression of the spring.

In some implementations, the one or more slotted tracks contains a first angled wall such that an initial compression of the spring results in the protruding slider to move along the inner circumference of the outer cylinder via the first angled wall, resulting in the needle cover to rotate along a central axis. Decompression of the spring after the initial compression results the protruding slider to move further along the inner circumference of the outer cylinder via a second angled wall resulting in the protruding slider to move into a hard corner that prevents further compression of the spring.

In some implementations, the positioning of the needle tip beyond the needle cover is approximately between 0.5 mm to 2.0 mm.

In some implementations, a fluid-filled syringe is in operable connection with the needle. The operable connection is a Luer lock.

In some implementations, the fluid within the fluid-filled syringe is a medication or a supplement for the skin.

In some implementations, the fluid within the fluid-filled syringe is triamcinolone, hyaluronic acid, collagen, or a collagen stimulating agent.

In some implementations, a method is for injecting a particular dose of fluid at a particular depth. The method comprises providing an injector system comprising a housing compartment comprising a flange holder system, a plunger retainer system, a fluid-filled syringe comprising a flange and a plunger, a needle assembly attached to the fluid-filled syringe, and an actuator of an injection mechanism that expels a controlled dose fluid. The method further comprises placing the needle assembly proximal to a site of injection. The method further comprises actuating the actuator resulting in the needle of the needle assembly inserting into the site of injection at a particular depth and the expulsion of a controlled dose of fluid from the fluid-filled syringe via the needle of the needle assembly.

In some implementations, a needle cap is for controlling the depth of insertion of a needle. The needle cap comprises a cylindrical tube having a proximal orifice on a proximal face and distal orifice opposite of the proximal orifice. The distal orifice is capable of fitting onto a base of a needle such that a tip of the needle inserts through the proximal orifice and is a particular distance from the proximal face.

BRIEF DESCRIPTION OF THE DRAWINGS

The description and claims will be more fully understood with reference to the following figures, which are presented as exemplary embodiments of the disclosure and should not be construed as a complete recitation of the scope of the disclosure.

FIGS. 24 and 25 provide illustrations of an exemplary electromechanical injector system in accordance with various embodiments.

DETAILED DESCRIPTION

Figure 1A:
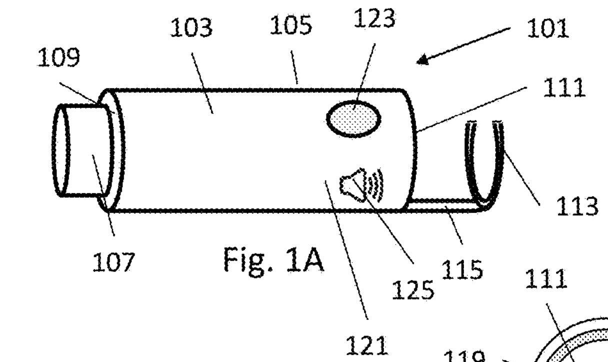
FIGS. 1A to 1C provide illustrations of injector devices in accordance with various embodiments of the disclosure.

Turning now to the drawings, systems, devices and methods for precise intradermal fluidic delivery utilizing needles or microneedles are described, in accordance with various embodiments of the disclosure. In certain embodiments, an intradermal or a subdermal fluidic system utilizes an injector device and a replaceable injection system. The injection system can comprise a cartridge with microneedle or a syringe with needle that can store a fluid (e.g., medication or supplement). In certain embodiments, a replaceable injection system is compatibly coupled with an injector device such that the mechanics of the injector is capable of ejecting the fluid out of the injection system through a microneedle or needle. In certain embodiments, a microneedle or needle is integrated with the cartridge or syringe as a single component. In certain embodiments, a microneedle or a needle and a cartridge or syringe are each an individual component capable of interlocking together (e.g., Luer lock connector).

In certain embodiments, an intradermal or subdermal delivery system is utilized for delivery of a medication and/or supplement, such as triamcinolone (Kenalog), hyaluronic acid, or collagen (or a collagen stimulating agent), which can be used in a variety of treatment applications for skin. For instance, in certain embodiments, an intradermal or subdermal delivery system delivers triamcinolone into an acne lesion as an acne treatment. In certain embodiments, an intradermal or subdermal delivery system delivers hyaluronic acid into the skin. And in certain embodiments, an intradermal or subdermal delivery system delivers collagen and/or a collagen producing agent into the skin, which can improve skin elasticity and appearance.

The described systems, devices, and methods should not be construed as limiting in any way. Instead, the present disclosure is directed toward all novel and nonobvious features and aspects of the various disclosed embodiments, alone and in various combinations and sub-combinations with one another. The disclosed systems, devices, and methods are not limited to any specific aspect, feature, or combination thereof, nor do the disclosed systems, devices, and methods require that any one or more specific advantages be present or problems be solved.

Various embodiments of intradermal or subdermal fluidic delivery systems and examples of fluidic delivery devices and cartridges are disclosed herein, and any combination of these options can be made unless specifically excluded. For example, any of the fluidic delivery devices disclosed, can be used with any type of compatible replaceable injection system, even if a specific combination is not explicitly described. Likewise, the different constructions and features of fluidic delivery systems can be mixed and matched, such as by combining any delivery system type/feature, delivery device type/feature, cartridge, etc., even if not explicitly disclosed. In short, individual components of the disclosed systems can be combined unless mutually exclusive or physically impossible.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

The terms "proximal" and "distal" as used throughout the description relate to a site of injection. Accordingly, a proximal face or proximal portion of a device is the face or the portion that would be more proximal to a site of injection when an injection is performed. Conversely, a distal face or distal portion of a device is the face or the portion that would be more distal to a site of injection when an injection is performed. Likewise, a proximal movement would be movement of a component in a direction towards a site of injection and a distal movement would be movement of a component in an opposite direction. Although these terms are in relationship to a site of injection, it is to be understood that these terms are used for reference and the site of injection does not need to be present when interpreting the components or movements of the devices and systems described herein.

Systems and Devices for Intradermal and Subdermal Micro-injection

Various embodiments are directed towards systems and devices for intradermal and/or subdermal injection. In certain embodiments, an intradermal and/or subdermal injection system includes an injector device, a cartridge or syringe, and a microneedle or needle. Generally, and in accordance with various embodiments described herein, an injector system is compatible with a fluid-filled replaceable injection system such that the injector is configured to receive and operatively link with the replaceable injection system. In certain embodiments, when an injector and replaceable injection system are operatively linked, the injector provides mechanics to eject liquid from the replaceable injection system through the needle. In certain embodiments, a microneedle or needle is integrated with the cartridge or syringe as a single component. In certain embodiments, a microneedle or a needle and a cartridge or syringe are each an individual component capable of interlocking together (e.g., Luer lock connector).

Injector Systems

In certain embodiments, an injector device is configured to provide mechanics for fluidic ejection out of a replaceable injection system. An injector can operate via mechanical or electromechanical means. In certain embodiments, an injector includes one or more actuators (e.g., buttons or triggers) to initiate and/or drive the mechanical and/or electrical components of the device. In certain embodiments, an actuator is mechanically or electrically operatively linked with an internal driver system that is operatively linked with a replaceable injection system to eject liquid out and through a needle. In certain embodiments, an internal driver system cooperatively interacts with a compression spring, which can help control the flow of fluidic ejection out of the cartridge and/or return the driver to an initial position. In certain embodiments, an actuator is operatively linked with an internal driver mechanism that is capable of driving the needle to pierce and situate within the skin for injection. In certain embodiments, an internal driver mechanism is a linear actuator utilizes one or more of: rotatable threaded rod, a worm gear, a rack and pinion, or a solenoid coil. In certain embodiments, a differential screw mechanism is utilized for fine micron (or less) movements.

In certain embodiments, an electromechanical injector device includes a power source or battery, such as (for example) a lithium ion battery, however any appropriate power source or batter can be utilized. In certain embodiments, an injector device includes a computation system and/or software to provide instructions on performing various tasks of the injector device. Various tasks to be performed include (but are not limited to) penetration of skin with a needle, ejection of components out of a replaceable injection system, retrieval of the needle out the skin, provide laser/light, calculation of dosage, calculation of volume to administer, calculation of needle depth for administration, camera image data (live or captured), storage of data, and connection with internet systems or other systems (e.g., Bluetooth, cloud systems, Wi-Fi enabled, cellular data enabled). Data that can be stored within a memory of the treatment device include (but are not limited to) procedure logs, cartridge logs (e.g., type, volume), location logs, dosage logs, and needle depth logs.

In certain embodiments, the needle remains unexposed to the user during the injection process. In certain embodiments, an injection device includes one or more sensors, which can be utilized to sense needle penetration, requisite needle depth, fluid ejection, local pressure, or any other appropriate sensation to be detected. In certain embodiments, an injection device in conjunction with a needle includes a sensor for measuring electrical impedance, which may be used to detect skin contact, needle penetration, and/or needle depth. In certain embodiments, a spacer on the needle system is provided to ensure proper needle penetration and depth.

In certain embodiments, an injector device includes housing for receiving a fluid-filled replaceable injection system (e.g., cartridge system or syringe system). In certain embodiments, a housing includes a reversible coupling and/or locking mechanism to facilitate the reception of the replaceable injection system. In certain embodiments, a replaceable injection system includes compatible components for coupling and/or locking with the injector. Any appropriate reversible coupling and/or locking mechanism can be utilized, such as (for example) a hook and with receiving groove, a flange, a threaded screw, a twist lock, a ball and lock pin, or any capable combination of coupling and/or locking mechanisms. In certain embodiments, a coupling and/or locking mechanism is reversible such that the replaceable injection system can be displaced from the replaceable injection system, in which displacement can occur prior to and/or after ejection of fluid.

In certain embodiments, an injector device includes a stabilizing feature (e.g., foot or base), which can be utilized to locate and/or stabilize the injector and needle system at a desired location on the skin. In certain embodiments, a stabilizing feature is extended from and connected to an injector system via a connector, which can be any appropriate connector such as a rod and/or strut. In certain embodiments, a stabilizing feature is the proximal face of an injector system housing. In certain embodiments, a stabilizing feature and a needle are cooperatively positioned such that the ejection tip of the needle is capable of extending beyond the stabilizing feature a requisite distance for intradermal or subdermal delivery. Human skin has a depth of approximately 0.5 mm to 5.0 mm, depending on the location. For instance, facial skin is approximately between 1.5 mm and 2 mm, and further varies on facial location (e.g., average thickness of forehead skin is approximately 1.7 mm and average thickness of cheek skin is approximately 1.85 mm). Accordingly, depending on location and use (e.g., intradermal or subdermal injection), in accordance with various embodiments, a needle tip is positioned between 0.5 mm to 5.0 mm beyond the stabilizing feature at time of injection. For uses on facial skin, in accordance with various embodiments, a needle or microneedle tip is positioned approximately between 0.5 mm to 2.0 mm beyond a stabilizing feature at time of injection. In various embodiments, a microneedle or needle tip is positioned approximately 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.5 mm, 3.0 mm, 3.5 mm, 4.0 mm, 4.5 mm, or 5.0 mm beyond the stabilizing feature at time of injection.

In certain embodiments, a housing of the injector system partially or entirely conceals the replaceable injection system. In certain embodiments, a housing further conceals a needle. In certain embodiments, a housing can include an orifice (e.g., pinhole) for the needle to be exposed during skin penetration. In certain embodiments, the proximal face of the housing surrounding the orifice can provide stabilizing and/or positioning effect at a desired location on the skin. In certain embodiments, the orifice and a needle are cooperatively positioned such that the ejection tip of the needle is capable of extending beyond the orifice a requisite distance for intradermal or subdermal delivery.

In certain embodiments, an injector system includes one or more cameras, which may be used to help visualize the treatment and/or record treatment sites images or data. Any appropriate camera can be utilized, including (but not limited to) visible light and infrared cameras. In certain embodiments, a camera is positioned proximal to a replaceable injection system such that it is capable of visualizing the treatment site and/or procedure. In certain embodiments, a light is utilized to enhance camera and/or user visualization. In certain embodiments, a laser is utilized to help guide a user to the proper injection site. In certain embodiments, a laser works in conjunction with a camera to provide precise treatment.

In certain embodiments, an injector system includes a means for providing feedback to ensure proper treatment. In certain embodiments, an injector system includes a means for providing feedback for when the replaceable injection system is securely within the device. In certain embodiments an injector system includes a means for providing feedback for when the replaceable injection system is not securely within the device. In certain embodiments, an injector system includes a means for providing feedback for when the injector system is ready for use. In certain embodiments, an injector system includes a means for providing feedback for when the injector system is actively providing treatment. In certain embodiments, an injector system includes a means for providing feedback for when the injector system has finished providing treatment. Any appropriate means for providing feedback can be utilized, including (but not limited to) a white light, a colored light, covering or uncovering of mechanical features on the device with and without use of color, and an audible sound.

Replacable Injection System

Several embodiments are directed towards interchangeable fluid-filled injection systems to be utilized in conjunction with an injector device. Replaceable injection systems include (but are not limited to) syringe systems and cartridge systems. In certain embodiments, a cartridge is a sealed container with fluid therein, which can be hermetically sealed. Any appropriate volume of fluid can be utilized. In various embodiments, a fluid-filled injection system contains approximately 0.01 cc to 1 cc. In various embodiments, a fluid-filled injection system contains approximately 0.01 cc, 0.05 cc, 0.1 cc, 0.15 cc, 0.2 cc, 0.25 cc, 0.3 cc, 0.35 cc, 0.4 cc, 0.45 cc, 0.5 cc, 0.55 cc, 0.6 cc, 0.65 cc, 0.7 cc, 0.75 cc, 0.8 cc, 0.85 cc, 0.9 cc, 0.95 cc, or 1.0 cc.

In certain embodiments, a replaceable injection system is for limited-use, such as single-use injection systems or multi-use injection systems. In various embodiments, a replaceable injection system contains fluid for one to ten injections. In certain embodiments, a replaceable injection system is disposable after liquid ejection. In certain embodiments, a replaceable injection system contains a plunger to facilitate ejection of liquid out of the cartridge and through a needle or microneedle.

In certain embodiments, a plunger of a replaceable injection system is capable of operatively linking with an internal driver of an injector device. In certain embodiments, an internal piston of an injector is capable of contacting a face of a replaceable injection system (e.g., a face opposite of a needle) such that the piston can operatively push a plunger of the injection system, resulting in ejection of liquid out of the injection system. In certain embodiments, a replaceable injection system is capable of operatively linking with an internal drive mechanism of an injector device such that the internal drive mechanism can move an injection system in an axial direction away and/or toward from a center portion of the injector. In certain embodiments, movement of a replaceable injection system via an internal drive mechanism of an injector simultaneously moves the ejection tip of a needle or microneedle and/or toward from a center portion of the injector, such that the internal drive mechanism operatively drives the needle or microneedle to pierce and insert into skin. In certain embodiments, an internal drive mechanism of an injector moves the ejection tip of a needle or microneedle to the requisite position beyond a stabilizing feature.

Needles and Microneedles

In certain embodiments, a needle or a microneedle is operatively linked with replaceable injection system such that fluid within the injection system can be expelled via the needle or microneedle. In certain embodiments, a needle or microneedle extends from a proximal face of the injection system (e.g., a face proximal to a site of injection when in use). In certain embodiments, a needle or microneedle is integrated with the replaceable injection system such that the needle or microneedle and injection system are a single component. In certain embodiments, a needle or microneedle and replaceable injection system are each an individual component capable of fitting together to ensure fluidic flow out of the injection system and through the needle or microneedle. Any appropriate means for fitting a needle or microneedle with a replaceable injection system can be utilized, such as (for example) a Luer lock system or a gasket.

In various embodiments, one or more needles or microneedles is operatively linked with a fluid-filled injection system such that fluid can be ejected out of the injection system via the one or more needles or microneedles. In certain embodiments, a single needle or microneedle is operatively linked with a fluid-filled cartridge. In certain embodiments, a plurality of needles or microneedles is operatively linked with a fluid-filled injection system, which can be arranged in an array, a regular pattern (e.g. circle), an irregular pattern, or any other configuration.

In some embodiments, a needle or microneedle has ability to provide a cooling effect, a heating effect, or a microvibration effect. Accordingly, a means to provide cooling, heating, or microvibration is operatively linked with the needle to provide the function. Any appropriate means for providing needles or microneedles with cooling, heating, or microvibration capability can be utilized.

In certain embodiments, one or more needles or microneedles are veiled or concealed, which may be desirable to prevent harm to a user from the needle or microneedle or for preventing damage to the needle or microneedle. Any appropriate means of veiling or concealing one or more needle or microneedles can be utilized. In certain embodiments, a covering is situated surrounding a microneedle. In certain embodiments, a covering is rigid and/or firm material. In embodiments utilizing a rigid and/or firm covering, the covering can unveil or reveal the microneedle through an orifice or pinhole, which can happen as it is advanced or prior to advancement into the injection site. In certain embodiments, a covering is collapsible and/or puncturable material such that a needle or microneedle is unveiled or revealed by the covering collapsing and/or the needle or microneedle puncturing through the covering. Puncturable material include (but are not limited to) rubber, neoprene, PTFE, ePTFE and metallic foil. In certain embodiments, after ejection of fluid out of the cartridge via a needle or microneedle, the needle or microneedle is re-veiled or re-concealed. In certain embodiments, a rigid or firm covering ejects outwards from the housing and covers the needle or microneedle after injection.

Exemplary Systems and Devices

Figure 1B:
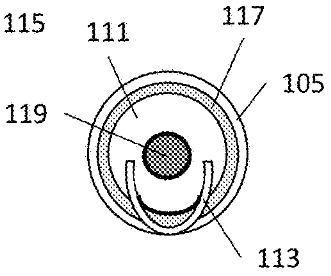
Figure 1C:
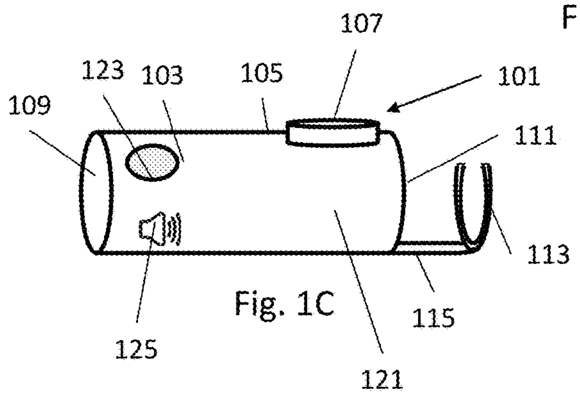

Turning now to FIGS. 1A to 1C, examples of an injector systems are provided, in accordance with various embodiments. As can be seen in FIGS. 1A, an injector 101 can include a body 103 with an external covering 105 that covers an internal piston. Injector 101 can include a button 107 that can initiate and/or drive the mechanics of the internal piston and an internal driver. As shown, button 107 is on a face 109 opposite of a face 111 that couples with a fluid-filled cartridge (not shown). Injector 101 can further include a stabilizing and/or position foot 113 that extends away from body 103 via a strut connector 115. As shown, stabilizing and/or positioning foot 113 extends away from face 111 capable of coupling with a fluid-filled cartridge. Injector 101 can also optionally include a light feedback indicator or window with colored components 123 and a sound feedback indicator 125 to provide feedback of one or more of the following: securement of the cartridge, ready for use, active engagement of treatment, finished providing treatment, or any other appropriate feedback.

Provided in FIG. 1B is a view of injector 101 showing face 111 that couples with a fluid-filled cartridge. Face 111 includes a coupling portion 117 for coupling the injector with a fluid-filled cartridge. Face 111 further shows an internal piston 119 that moves in axial direction away and towards from a central portion 121 of the body.

FIG. 1C provides another example an injector 101 in which button 107 extends from a curved face of cylindrical body 103.

Figure 2A:
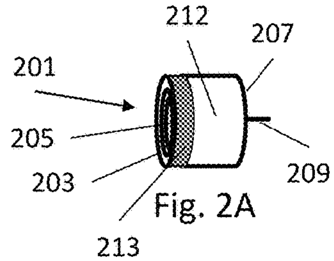
FIGS. 2A to 4B provide illustrations of fluid-filled cartridges in accordance with various embodiments of the disclosure.
Figure 2B:
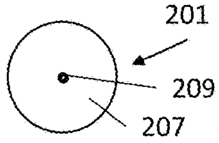
Figure 3A:
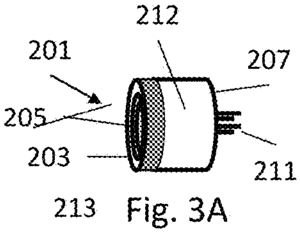
Figure 3B:
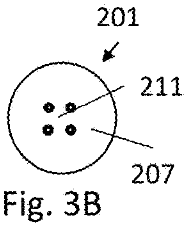

FIGS. 2A to 4B provide various examples of fluid-filled cartridges 201, in accordance with various embodiments. As can be seen within these figures, a cartridge can include a face 203 capable of coupling with an injector, including a central portion 205 that can interact with an internal piston of the injector. Opposite of face 203 capable of coupling with an injector is a face 207 with one or more microneedles. As seen in FIGS. 2A and 2B, a single microneedle 209 can be utilized. Alternatively, as seen in FIGS. 3A and 3B, a plurality of microneedles 211 can be utilized, which can be in for the form of an array (e.g., 2×2), a pattern (e.g., a circle), or an irregular pattern, each microneedle having a microneedle ejection tip. Within cartridge 201 is a plunger 213 and a fluid-filled portion 212 that stores fluid until it is ejected from the cartridge. Plunger 213 can interact with central portion 205 of face 203, which can interact with an internal piston of the injector such that the plunger can moved in axial direction away from face 203 and towards the one or more microneedles 209/211. Cartridge 201 includes a fluid-filled portion 212 that stores fluid until it is ejected from the cartridge.

Figure 4A:
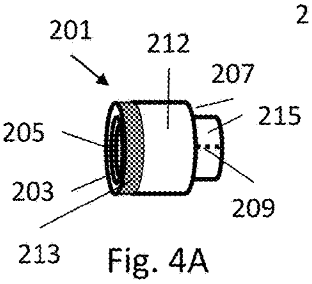
Figure 4B:
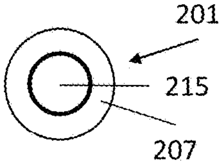

FIGS. 4A and 4B provide an example of a covering 215 that veils and/or conceals one or more needles (only a single needle 209 is portrayed as dashed lined), in accordance with various embodiments. Covering 215 can surround the one more needles to provide concealment. The covering can include one or more pinholes (not shown) that can allow for exposure of the one or more concealed needles as they advance through the pinholes. Alternatively, the cover can be of a puncturable material such that the one or more needles can be exposed by puncturing through material as they are advanced.

Figure 5A:
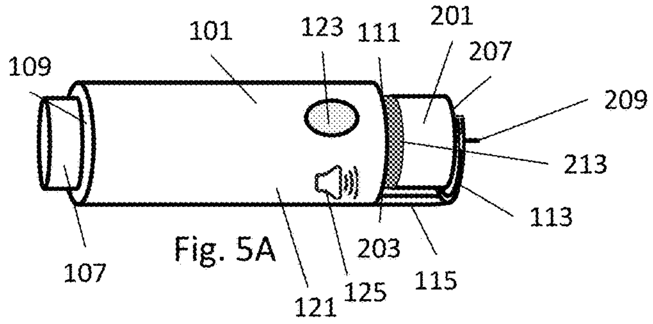
FIGS. 5A to 5D provide illustrations of injector systems in accordance with various embodiments of the disclosure.
Figure 5B:
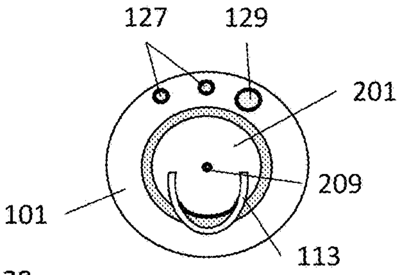
Figure 5C:
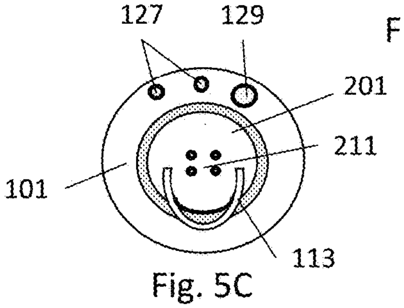
Figure 5D:
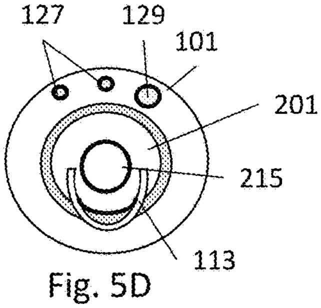

Provided in FIGS. 5A to 5D are the exemplary injector device 101 of FIG. 1A operatively linked with the exemplary fluid-filled cartridges 201 of FIGS. 2A to 4B, in accordance with various embodiments. As can be seen in FIG. 5A, fluid cartridge 201 can situate within injector 101 such that face 203 of cartridge 201 is in contact with face 111 of the injector 101. Central portion 205 of face 203 of the cartridge interacts with internal piston 119 of the injector 101. Further, microneedle 209 extends in a direction away from injector 101 and is positioned such that microneedle ejection tip 210 is advanced beyond foot 113. As discussed previously, the precise position the microneedle tip in reference to the foot depends on the desired type of delivery (e.g., intradermal or subdermal) and the thickness of the skin at the injection site. FIGS. 5B to 5D show a view of face 207 of cartridge 201 situated in injector 101. Injector 101 can also optionally include a light feedback indicator or window with colored components 123 and a sound feedback indicator 125 to provide feedback of one or more of the following: securement of the cartridge, ready for use, active engagement of treatment, finished providing treatment, or any other appropriate feedback. Further, device 101 can incorporate one or more cameras 127 and visualization light 129, which may be used to assist and/or record use of the device and cartridge.

Figure 6A:
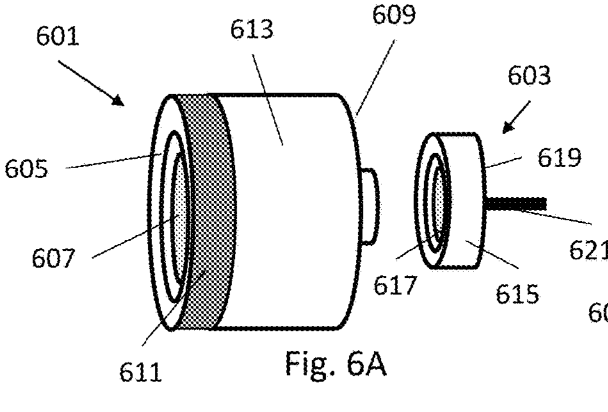
FIGS. 6A and 6B provide illustrations of cartridges and microneedles as discrete components in accordance with various embodiments of the disclosure.
Figure 6B:
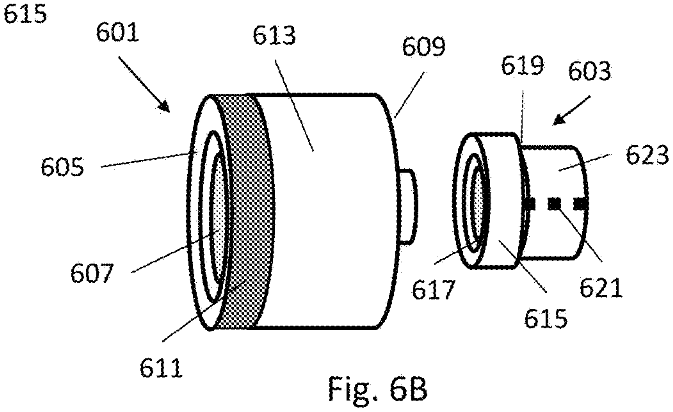

FIGS. 6A and 6B provide examples of a cartridge component 601 and microneedle component 603 as individual components that can be assembled together, in accordance with various embodiments. Cartridge 601 includes a face 605 capable of coupling with an injector, including a central portion 607 that can interact with an internal piston of the injector. Opposite of face 605 capable of coupling with an injector is a face 609 capable of coupling with a microneedle assembly 603. Within cartridge 601 is a plunger 611 and a fluid-filled portion 613 that stores fluid until it is ejected from the cartridge. Plunger 611 can interact with central portion 607 of face 605, which can interact with an internal piston of the injector such that the plunger can moved in axial direction away from face 605 and towards the microneedle assembly 603.

Microneedle component 603 includes a base 615 with a face 617 capable of coupling with face 609 of cartridge 601. The coupling can be any appropriate coupling that allows for adequate fluid from the cartridge and into the microneedle assembly, such as (for example) a Luer lock or gasket. Opposite of face 617 is a face 619 with a microneedle 621 that extends away from the microneedle assembly base 615. Although not shown, a microneedle assembly can include a plurality of microneedles, which can be formed into an array or any other appropriate pattern. As shown in FIG. 6B, a microneedle assembly 603 can include a covering 623 that veils and/or conceals one or more needles (only a single needle 621 is portrayed as dashed lined). Covering 623 can surround the one or more needles to provide concealment. The covering can include one or more pinholes (not shown) that can allow for exposure of the one or more concealed needles as they advance through the pinholes. Alternatively, the cover can be of a puncturable material such that the one or more needles can be exposed by puncturing through material as they are advanced.

Figure 7:
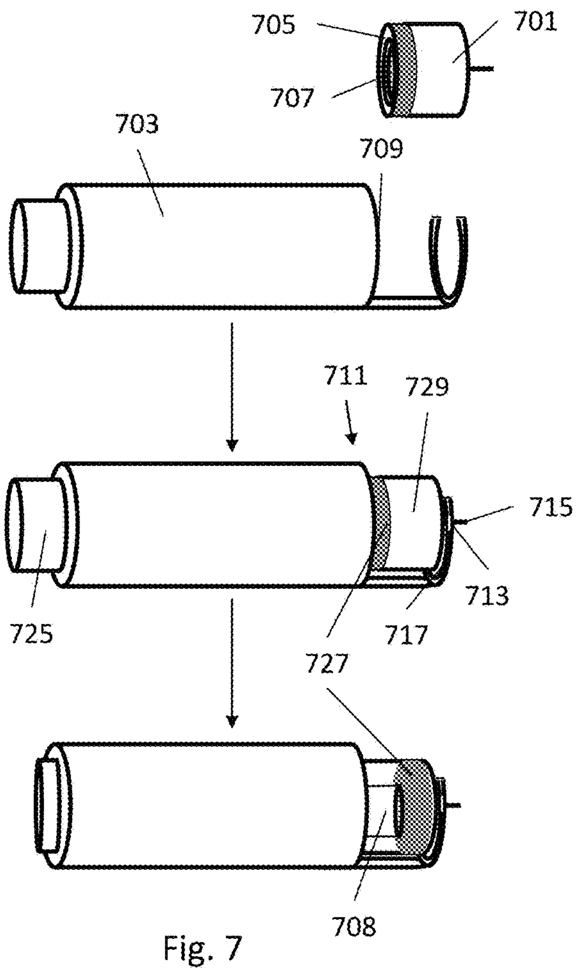
FIGS. 7 to 9 provide illustrations of mechanics of injector systems with unassisted penetration in accordance with various embodiments of the disclosure.
Figure 8:
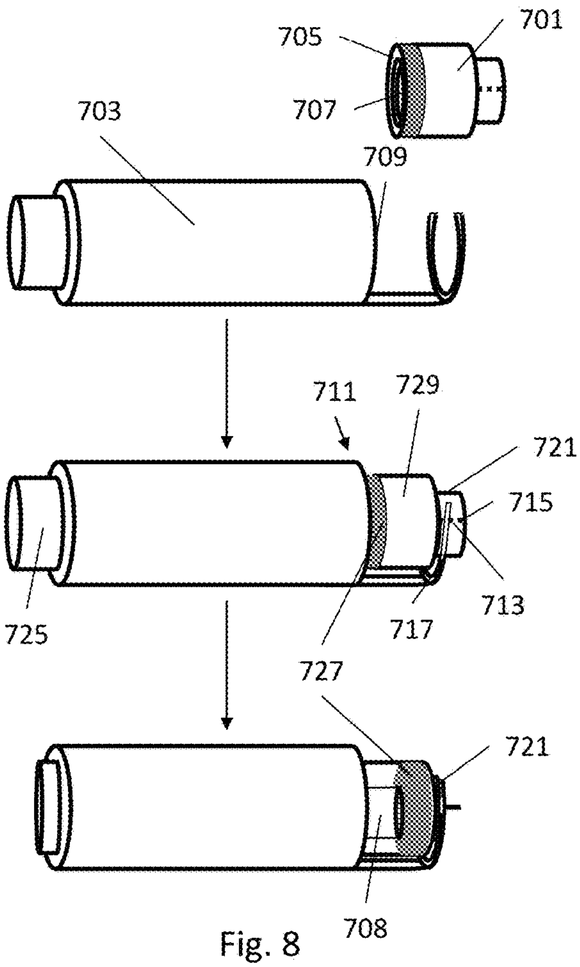
Figure 9:
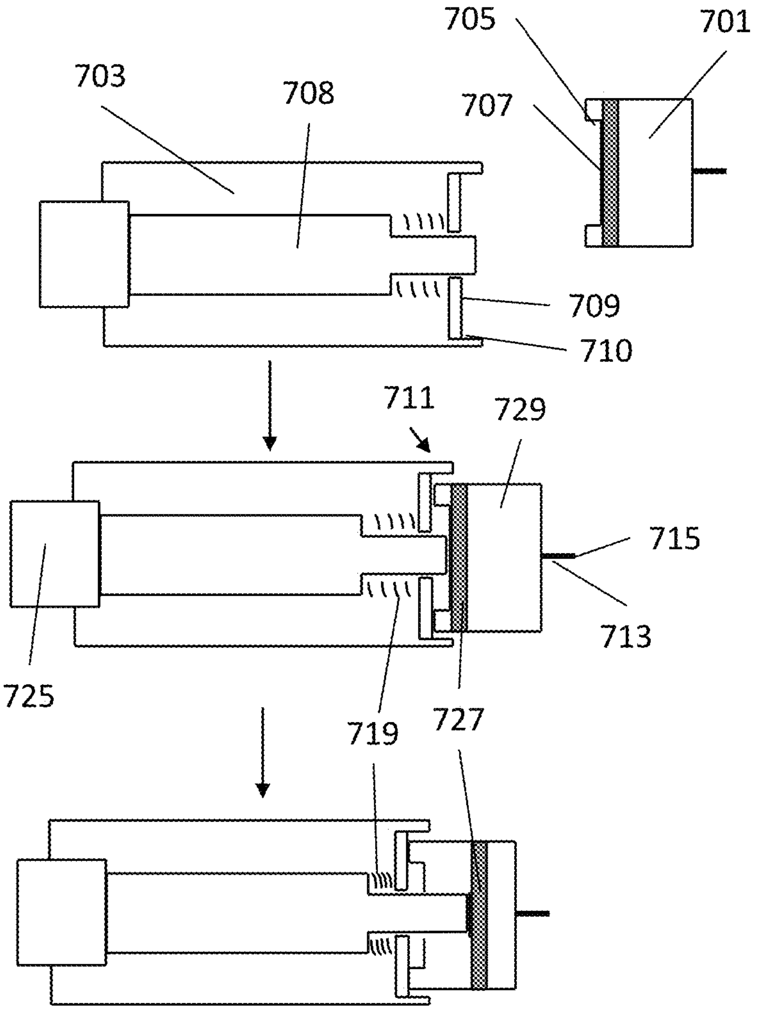

Provided in FIGS. 7 to 9 are examples of injector systems with unassisted skin penetration, in accordance with various embodiments. A cartridge 701 is loaded onto an injector device 703. Cartridge 701 includes a face 705 with a central portion 707 cooperatively couples with a face 709 and internal piston 708 of injector device 703. The outer portion 710 of face 709 includes a reversible coupling and/or locking mechanism to facilitate the reception of face 705 of cartridge 701. Coupling of cartridge 701 with injector device 703 results in an injector system 711. Assembled injector system 711 includes a microneedle 713 extends in a direction away from the injector device 703. Assembly of injector system 711 results in a microneedle ejection tip 715 that is appropriately positioned in relationship to a foot 717 such that the ejection tip extends beyond the foot a requisite distance for intradermal or subdermal injection. Note, for sake of simplicity and explanation, FIG. 9 does not show a foot but it can be assumed one is present on the assembled system. Microneedle 713 can be concealed utilizing a covering 721 as shown in FIG. 8.

Assembled injector system 711 can be used for intradermal or subdermal injection of liquid. A user can penetrate skin with microneedle ejection tip 715 at a desired location, moving microneedle 713 perpendicular to the surface of the skin and penetrating into the skin until foot 717 rests upon the outer surface of the skin, resulting in the microneedle tip having the requisite depth for proper intradermal or subdermal injection. With proper depth, injector system 711 can inject liquid into the skin. Covering 721 can be pierceable or include a pinhole such that microneedle 713 can be exposed to penetrate the user's skin. As shown in FIG. 8, covering 721 is collapsible such that as the needle penetrates the user's skin, it collapses until the needle reaches the requisite depth for proper intradermal or subdermal injection, resulting in a collapsing of covering 721. As noted herein, a covering can be retractable and/or removable instead of being collapsible.

Injector system 711 utilizes a spring 719 that is operative with internal piston 708 to facilitate liquid ejection. A button 725 is utilized to move piston 708 in an axial direction towards cartridge 701. As piston 708 moves in the axial direction, the piston interacts with center portion 707 of face 705, pushing the center portion in the axial direction and towards microneedle 713. Center portion 707 interactions with a plunger 727 to displace liquid within a liquid containing portion 729 of cartridge 701, resulting in liquid passing through microneedle 713 and out of ejection tip 715. After injection of liquid into the skin, microneedle 713 can be removed the skin. Multi-use cartridges can be utilized for multiple injections and the steps to inject liquid into another desired location can be repeated. After cartridge 701 is spent, it can be removed and disposed and injector device 703 can be reused with a subsequent cartridge.

Figure 10:
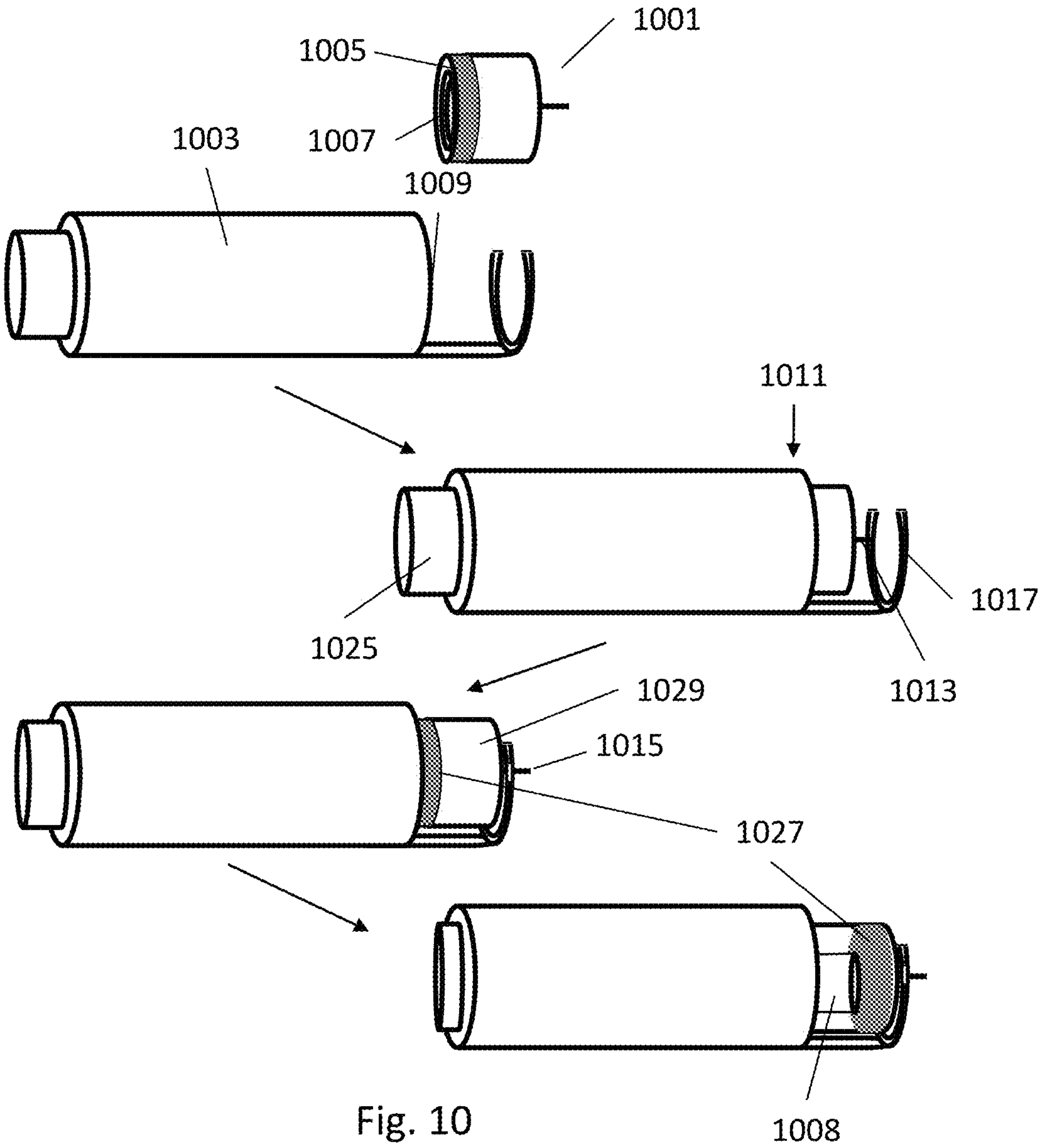
FIGS. 10 to 12 provide illustrations of mechanics of injector systems with assisted penetration in accordance with various embodiments of the disclosure.
Figure 11:
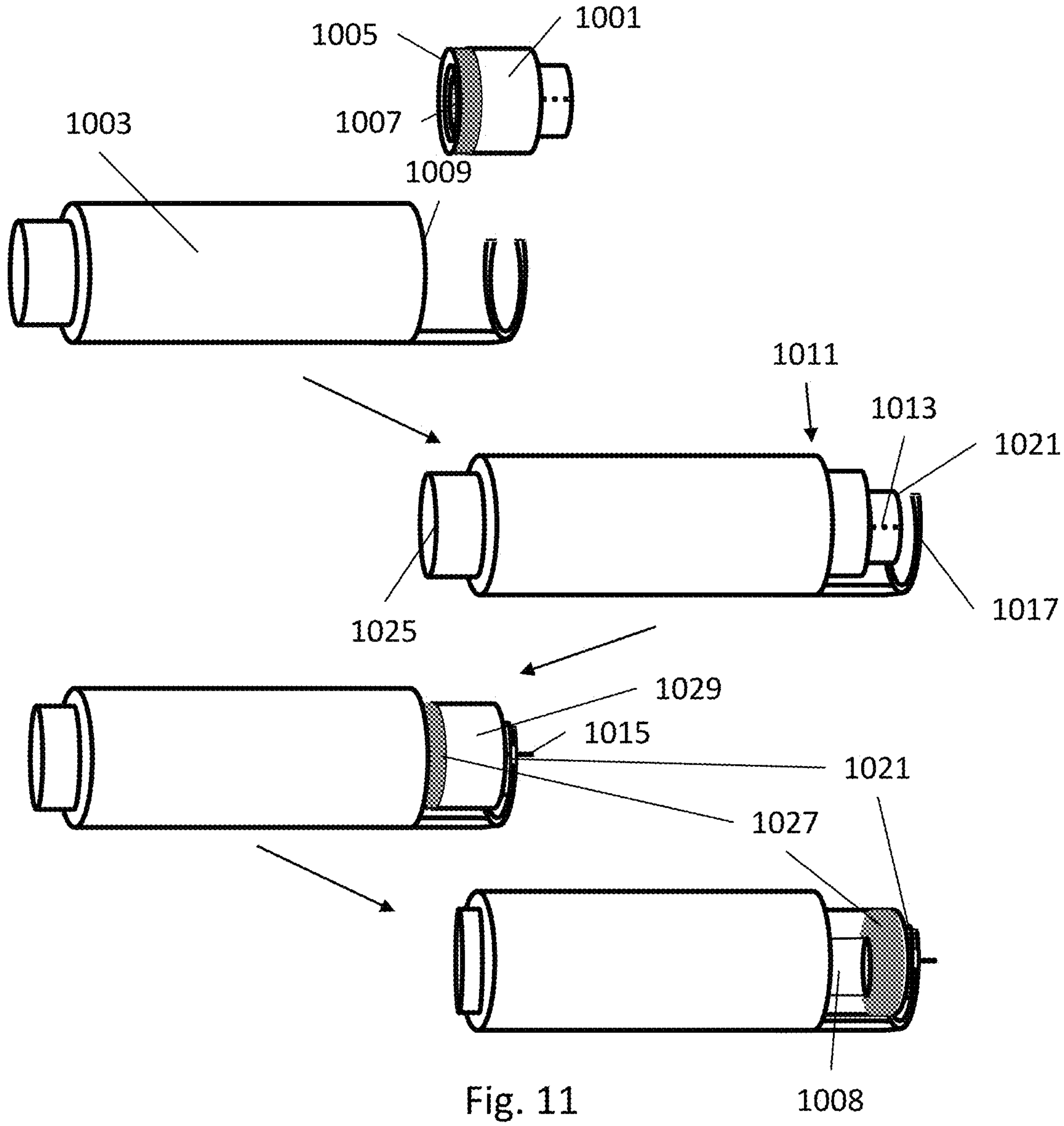
Figure 12:
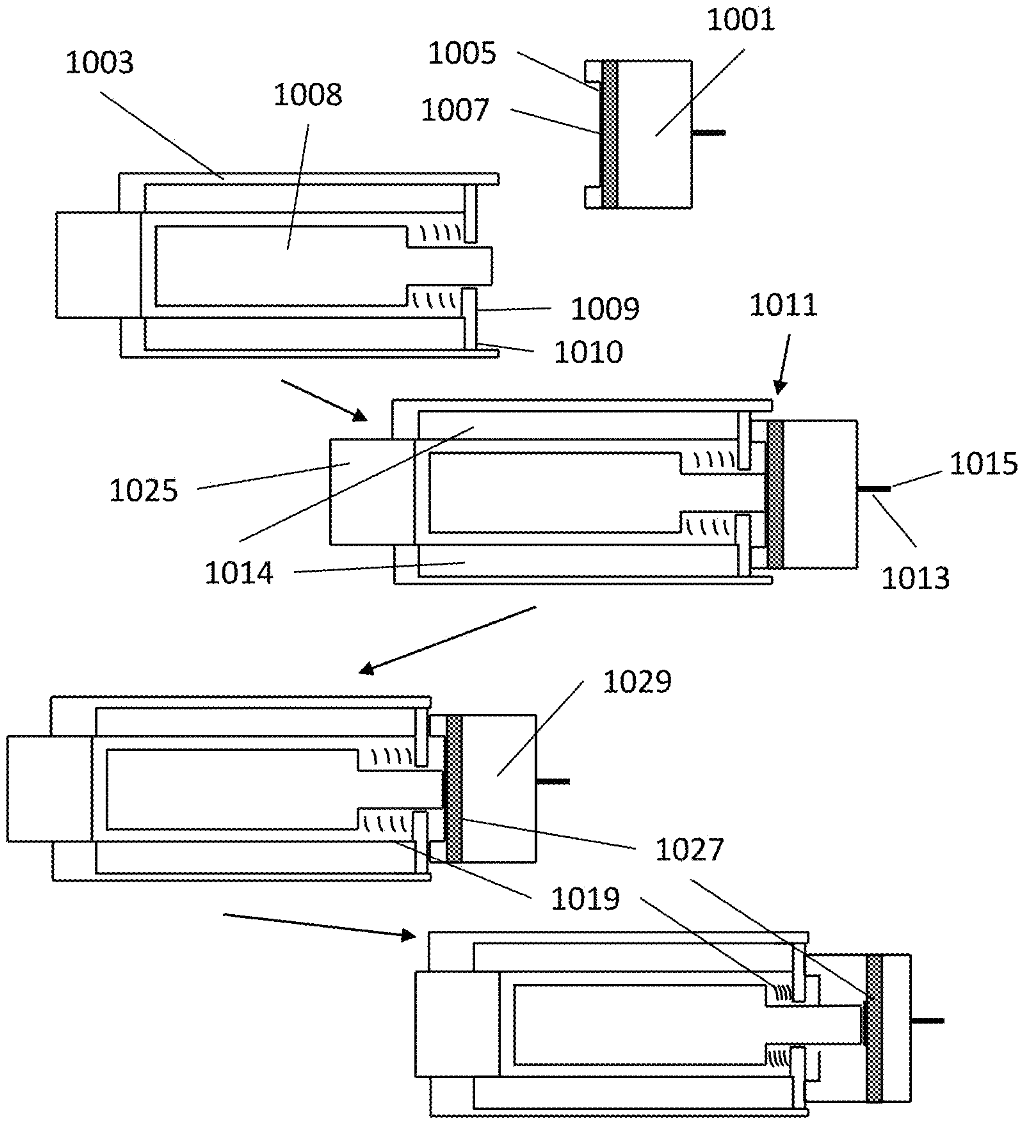

Provided in FIGS. 10 to 12 are examples of injector systems with assisted skin penetration, in accordance with various embodiments. A cartridge 1001 is loaded onto an injector device 1003. Cartridge 1001 includes a face 1005 with a central portion 1007 cooperatively couples with a face 1009 and internal piston 1008 of injector device 1003. The outer portion 1010 of face 1009 includes a reversible coupling and/or locking mechanism to facilitate the reception of face 1005 of cartridge 1001. Outer portion 1010 further includes an operative link with an internal driver 1014 that facilitates assisted skin penetration. Coupling of cartridge 1001 with injector device 1003 results in an injector system 1011. Assembled injector system 1011 includes a microneedle 1013 extends in a direction away from the injector device 1003. Assembly of injector system 1011 results in a microneedle ejection tip 1015 that is slightly recessed from a requisite distance for intradermal or subdermal injection. As shown in FIGS. 10 and 11, ejection tip 1015 in slightly recessed in relationship to a foot 1017, which can allow for a user to position injector system 1011 utilizing foot 1017 prior to penetrating skin with microneedle 1013. Note, for sake of simplicity and explanation, FIG. 12 does not show a foot but it can be assumed one is present on the assembled system. Microneedle 1013 can be concealed utilizing a covering 1021 as shown in FIG. 11.

Assembled injector system 1011 can be used for intradermal or subdermal injection of liquid. Once a user positions injector system 1011, the system can assist the user to penetrate their skin with microneedle ejection tip 1015 at a desired location. The user can push a button 1025 to initiate internal driver 1014, thus moving microneedle 1013 perpendicular to the surface of the skin and penetrating into the skin until ejection tip 1015 requisite depth for proper intradermal or subdermal injection. As shown in FIG. 12, internal driver 1014 is a one or more rigid outer members, such as one or more struts or sheath encircling inner piston 1008. Button 1025 can push internal driver 1014 in an axial direction towards cartridge 1001, resulting in the outer portion 1010 of face 1009 pushing the cartridge in the axial direction. As cartridge 1001 moves axially, microneedle 1013 penetrates the user skin until ejection tip 1015 reaches proper depth. With proper depth, injector system 1011 can inject liquid into the skin. Covering 1021 can be pierceable or include a pinhole such that microneedle 1013 can be exposed to penetrate the user's skin. As shown in FIG. 11, covering 1021 is collapsible such that as the needle penetrates the user's skin, it collapses until the needle reaches the requisite depth for proper intradermal or subdermal injection, resulting in a collapsing of covering 1021. As noted herein, a covering can be retractable and/or removable instead of being collapsible.

Injector system 1011 utilizes a spring 1019 that is operative with internal piston 1008 to facilitate liquid ejection. Button 1025 is utilized to move piston 1008 in an axial direction towards cartridge 1001. Alternatively, a second button can be utilized to facilitate movement of the piston in the axial direction. As piston 1008 moves in the axial direction, the piston interacts with center portion 1007 of face 1005, pushing the center portion in the axial direction and towards microneedle 1013. Center portion 1007 interactions with a plunger 1027 to displace liquid within a liquid containing portion 1029 of cartridge 1001, resulting in liquid passing through microneedle 1013 and out of ejection tip 1015. After injection of liquid into the skin, microneedle 1013 can be removed the skin. Multi-use cartridges can be utilized for multiple injections and the steps to inject liquid into another desired location can be repeated. After cartridge 1001 is spent, it can be removed and disposed and injector device 1003 can be reused with a subsequent cartridge.

Figure 13:
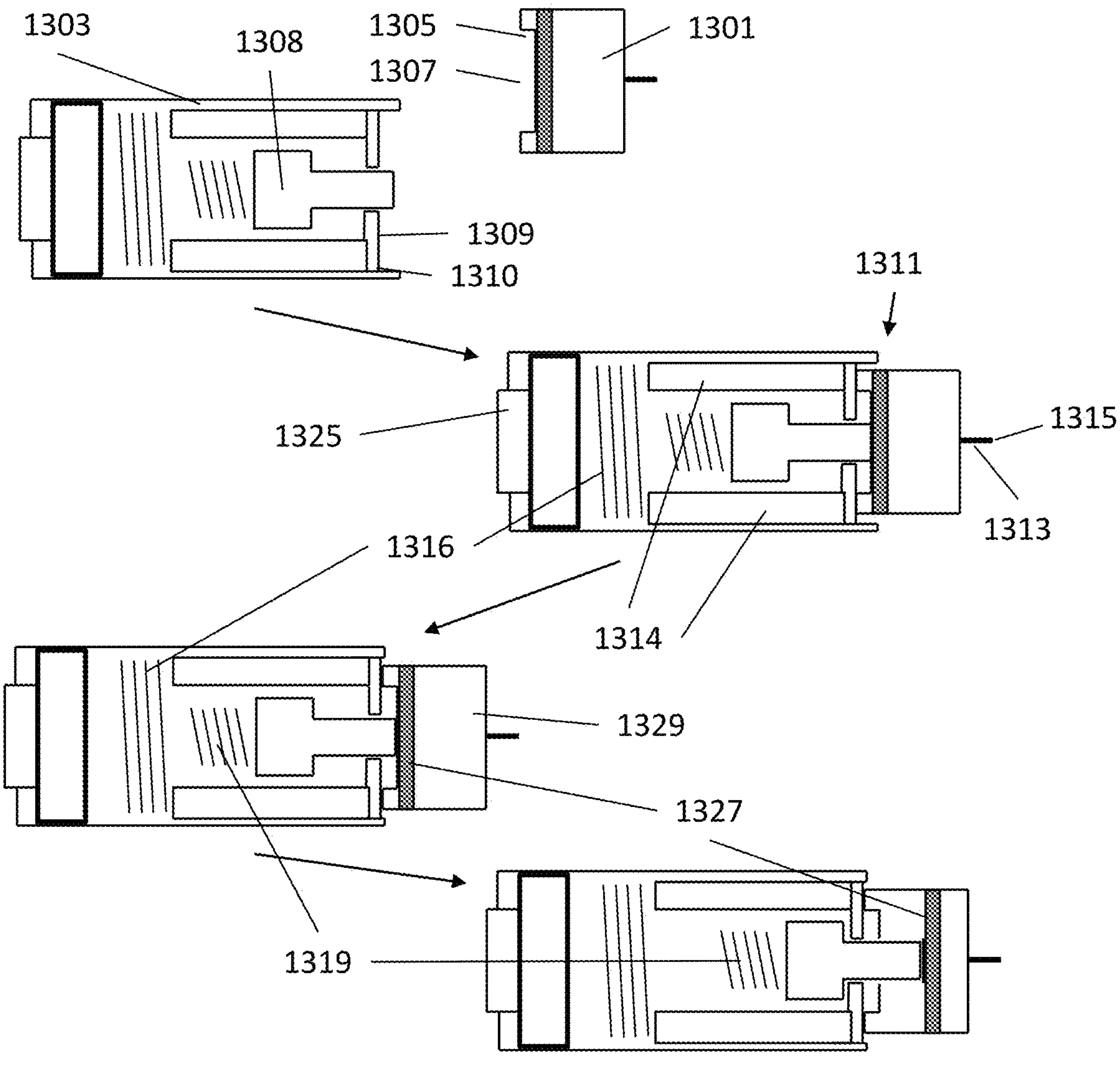
FIG. 13 provides illustrations of mechanics of electromechanical injector systems with assisted penetration in accordance with various embodiments of the disclosure.

Provided in FIG. 13 is an example of an electromechanical or dual spring injector system with assisted skin penetration, in accordance with various embodiments. A cartridge 1301 is loaded onto an injector device 1303. Cartridge 1301 includes a face 1305 with a central portion 1307 cooperatively couples with a face 1309 and internal piston 1308 of injector device 1303. The outer portion 1310 of face 1309 includes a reversible coupling and/or locking mechanism to facilitate the reception of face 1305 of cartridge 1301. Outer portion 1310 further includes an operative link with an internal driver 1314 that facilitates assisted skin penetration. Coupling of cartridge 1301 with injector device 1303 results in an injector system 1311. Assembled injector system 1311 includes a microneedle 1313 extends in a direction away from the injector device 1303. Assembly of injector system 1311 results in a microneedle ejection tip 1315 that is slightly recessed from a requisite distance for intradermal or subdermal injection. Note, for sake of simplicity and explanation, FIG. 13 does not show a foot but it can be assumed one is present on the assembled system. Microneedle 1313 can be concealed utilizing a covering.

Assembled injector system 1311 can be used for intradermal or subdermal injection of liquid. Once a user positions injector system 1311, the system can assist the user to penetrate their skin with microneedle ejection tip 1315 at a desired location. The user can push a button 1325 to initiate rotatable threaded rod or release a spring 1316 that is operatively linked with internal driver 1314. Electromechanical devices can be powered by a battery or other power source. Initiation of internal driver 1314 moves microneedle 1313 perpendicular to the surface of the skin and penetrating into the skin until ejection tip 1315 requisite depth for proper intradermal or subdermal injection. Internal driver 1314 is a one or more rigid outer members, such as one or more struts or sheath encircling inner piston 1308. Rotatable threaded rod or releasable spring 1316 can push internal driver 1314 in an axial direction towards cartridge 1301, resulting in the outer portion 1310 of face 1309 pushing the cartridge in the axial direction. As cartridge 1301 moves axially, microneedle 1313 penetrates the user skin until ejection tip 1315 reaches proper depth. With proper depth, injector system 1311 can inject liquid into the skin.

Injector system 1311 utilizes a second rotatable rod or releasable spring 1319 that is operative with internal piston 1308 to facilitate liquid ejection. Button 1025 is utilized to initiate rotation of rod or release of spring 1319 to move piston 1308 in an axial direction towards cartridge 1301. As piston 1308 moves in the axial direction, the piston interacts with center portion 1307 of face 1305, pushing the center portion in the axial direction and towards microneedle 1313. Center portion 1307 interactions with a plunger 1327 to displace liquid within a liquid containing portion 1329 of cartridge 1301, resulting in liquid passing through microneedle 1313 and out of ejection tip 1315. After injection of liquid into the skin, microneedle 1313 can be removed the skin. Multi-use cartridges can be utilized for multiple injections and the steps to inject liquid into another desired location can be repeated. After cartridge 1301 is spent, it can be removed and disposed and injector device 1303 can be reused with a subsequent cartridge.

Figure 14:
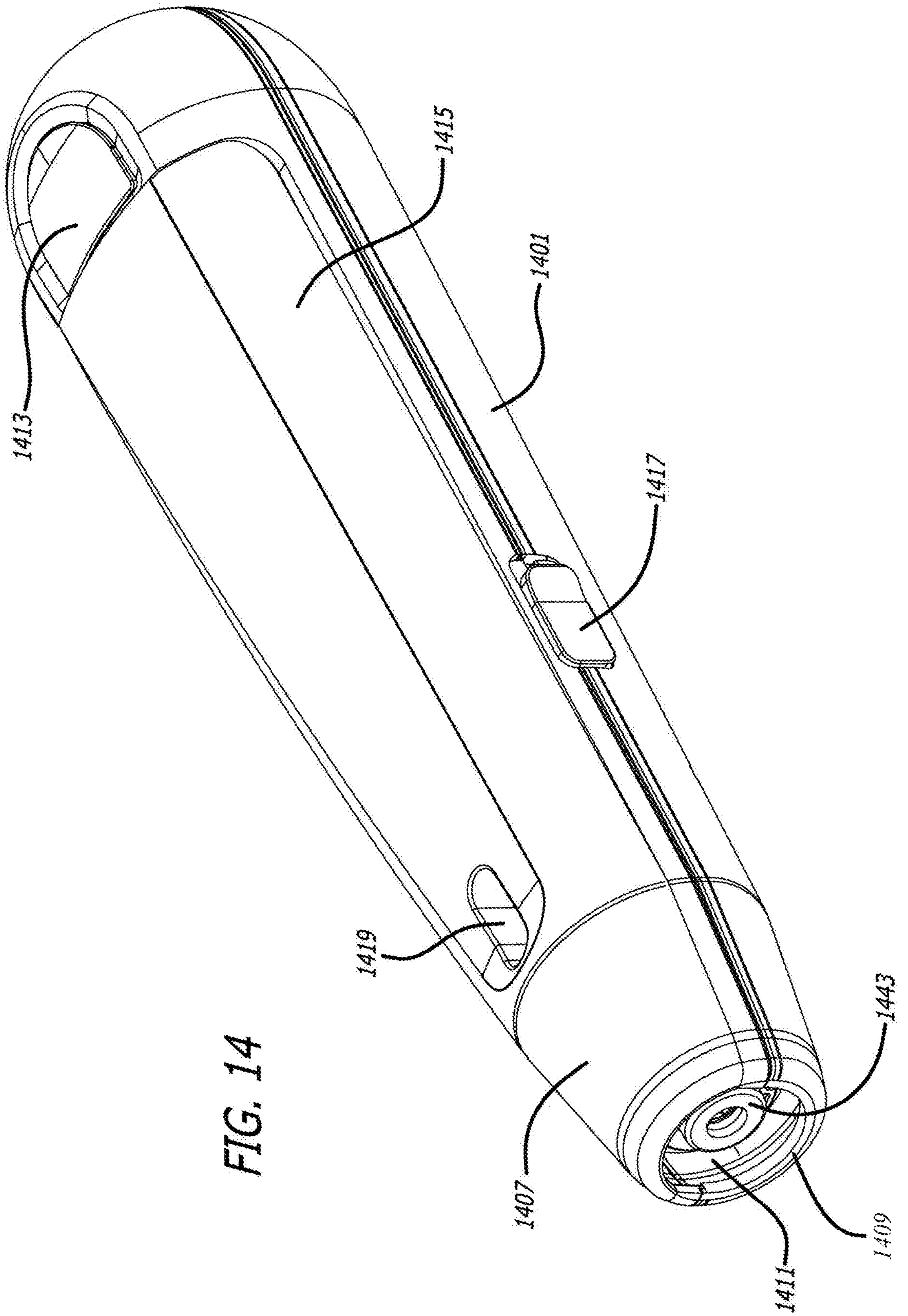
FIGS. 14 to 16B provide illustrations of an exemplary injector system in accordance with various embodiments.
Figure 15:
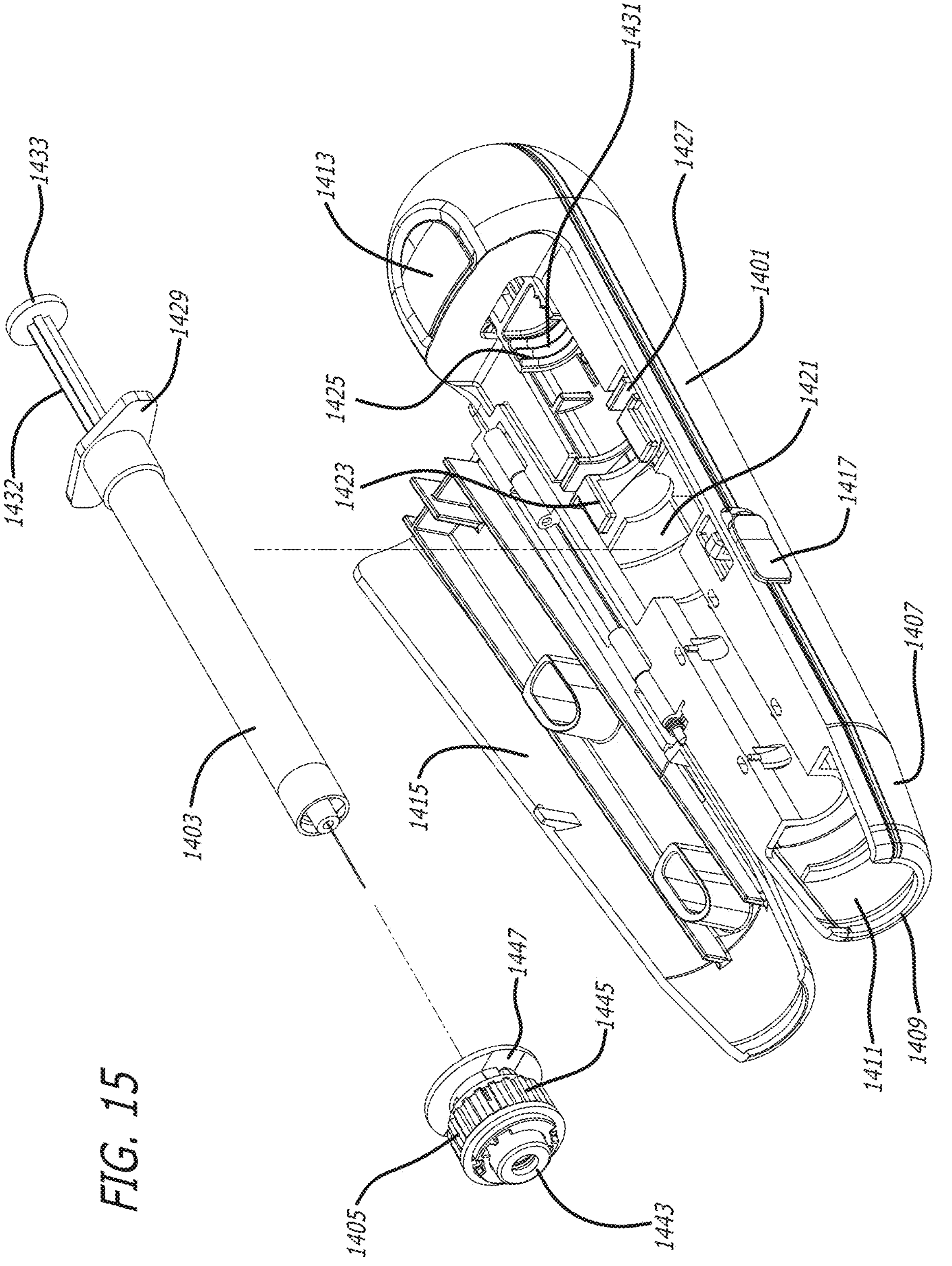
Figure 16A:
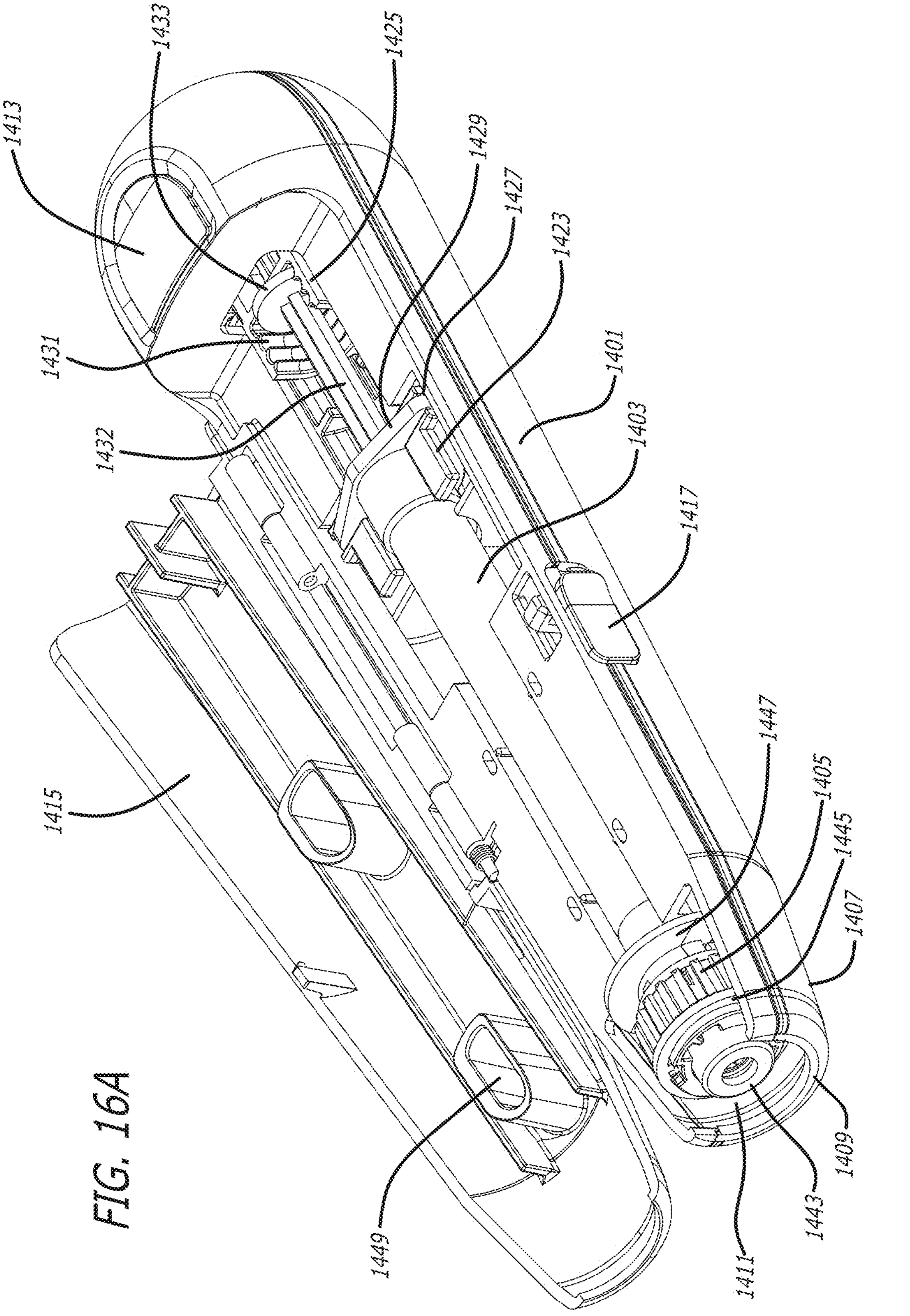
Figure 16B:
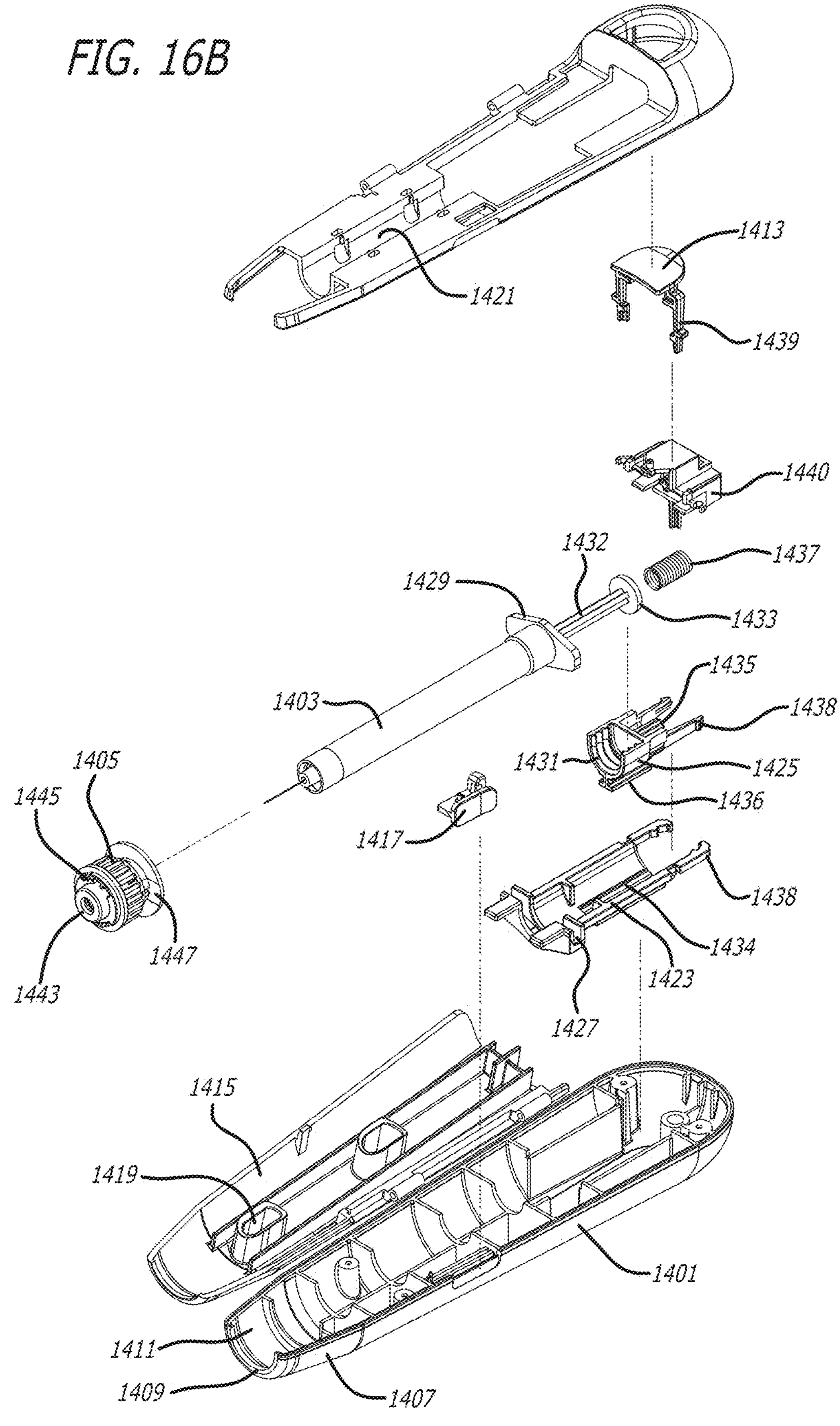

Provided in FIGS. 14 to 16B is an exemplary system for performing intradermal or subdermal injection of a liquid. The system as shown comprises a housing compartment 1401, a fluid-filled syringe 1403, and a needle assembly 1405. FIG. 14 shows the housing compartment 1401 in its closed state. FIG. 15 shows housing 1401 with lid 1415 in the open position. And FIGS. 16A and 16B show fluid-filled syringe 1403 and needle assembly 1405 installed within housing compartment 1401.

Housing compartment 1401 contains a proximal portion 1407 that is associated with needle assembly 1405 and provides a proximal face 1409 for contacting with skin when performing injection and an orifice 1411 to allow for injection. Housing compartment 1401 further contains a button 1413 for actuating an injection mechanism. A lid 1415 is provided with a latch 1417 that can open to allow for situating fluid-filled syringe 1403 and needle assembly within housing 1401. A window 1419 is provided for viewing the fluid-filled syringe 1403 and volume of fluid therein.

Needle assembly 1405 can connect with fluid-filled syringe 1403 by any appropriate means, such as a Luer lock. A connected fluid-filled syringe 1403 and needle assembly 1405 can be received by the housing 1401, which can contain a contoured indentation 1421 that conforms to the connected fluid-filled syringe 1403 and needle assembly 1405. Within housing 1401 are a syringe flange holder 1423 and plunger retainer 1425. Flange holder 1423 contains an indentation 1427 that is contoured to the shape of the syringe flange 1429 such that the syringe flange and snugly fit within the indentation. Likewise, plunger retainer 1425 contains a plurality of indentations 1431 each of which are contoured to the shape of plunger grip 1433 at the distal end of plunger 1432 such that the plunger grip and fit within one of the indentations. The plurality indentations allow for flexibility of plunger grip location which may vary depending on the volume of fluid within the syringe and the dose of fluid to be expelled.

Flange holder 1423 and plunger retainer 1425 each are movable in either a proximal direction or a distal direction along a central axis. Flange holder 1423 contains a groove 1434 that cooperates with slider 1436 of plunger retainer 1425. Groove 1434 and slider 1436 allow for plunger retainer 1425 capability to slide in either direction along the groove, independent of movement of flange holder 1423. Syringe flange holder 1423 and plunger retainer 1425 connect with each other via a latch 1438, and the plunger retainer contains a driver 1435 in operable connection with a compressed spring 1437 to provide the driving force for the injection mechanism. Spring 1437 is held in place by a distal base 1440 at the distal end of the system. Button 1413 contains two inward protruding struts 1439 that hold driver 1435 in place and spring 1437 in a compressed state. When button 1413 is pressed inward, inward protruding struts 1439 move along with the button in an inward direction, releasing the compression of spring 1437 to provide a force for driver 1435 to drive flange holder 1423 and plunger retainer 1425 in direction toward proximal portion 1407 along the central axis.

Needle assembly 1405 comprises a needle 1441. In some implementations, the needle assembly further comprises a protective cover 1443, an outer cylinder 1445, and an actuator ring 1447. Protective cover 1443 can prevent exposure of needle 1441 before and after injection, preventing the ability of the needle to prick or cause injury when not performing injection. Outer cylinder 1445 can provide a means to grip needle assembly 1405 and can further help facilitate ensuring protective cover 1443 adequately covers needle 1441. Actuator ring 1447 can unlock a mechanism for re-covering of protective cover 1443 over needle 1441 after injection. It should be understood that the needle assembly can be a standard needle without a protective cover, an outer cylinder, and an actuator ring. In some implementations, when used in housing compartment 1401 the length of the needle is such that when performing fluid injection, the tip of the needle extends beyond proximal face 1409 to control needle depth at the site of injection. In some implementations, the needle has a length such that controlled intradermal injection can be performed. In some implementations, a needle cap is used with the needle to control the depth of penetration into the site of injection (see FIGS. 30A and 30B on exemplary needle caps).

FIGS. 17A to 20 provide an example of various states of a system performing intradermal or subdermal liquid delivery. As described in reference to FIGS. 14 to 16B, the system comprises a housing compartment 1401, a fluid-filled syringe 1403, and a needle assembly 1405. Needle assembly 1405 is attached to fluid-filled syringe 1403 and fitted within housing compartment 1401. Specifically, syringe flange 1429 is situated within flange holder 1423 and plunger grip 1433 is situated within plunger retainer 1425, securing fluid-filled syringe 1403 within the housing.

Figure 17A:
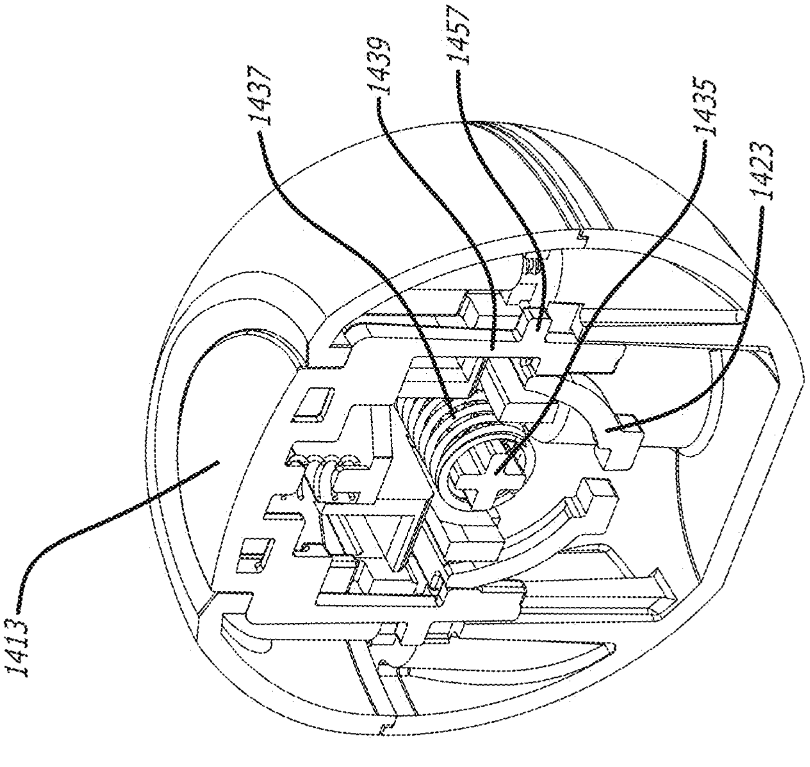
Figure 17B:
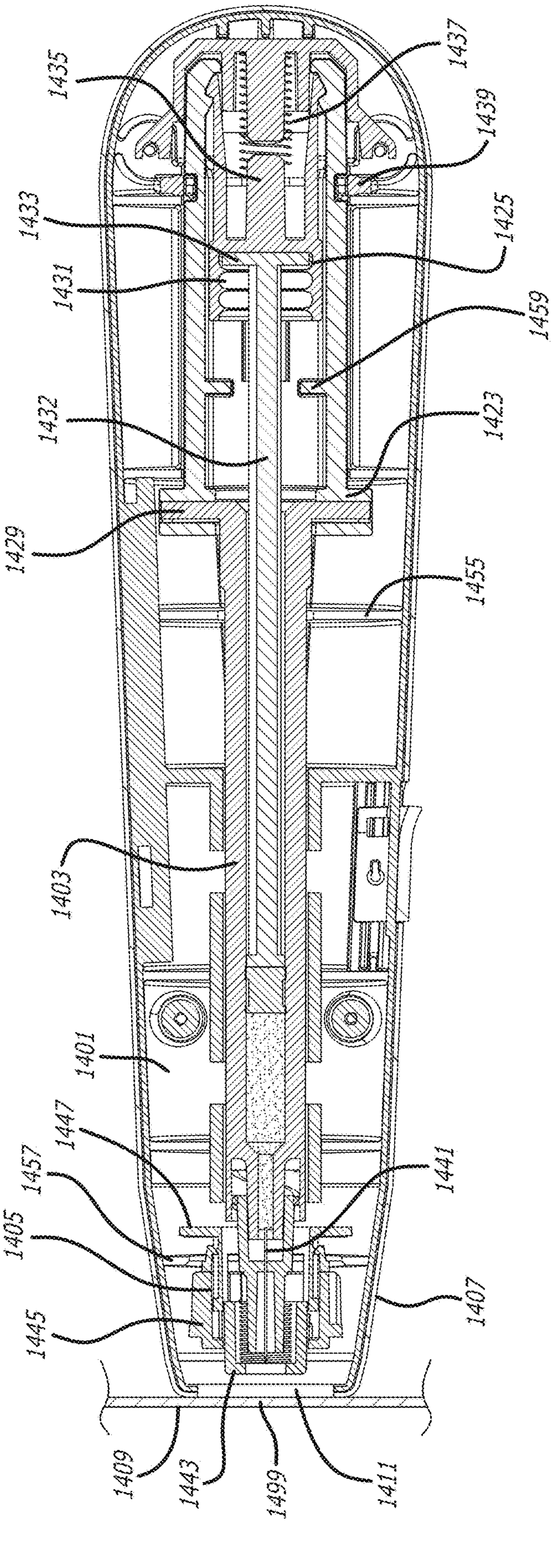

FIGS. 17A and 17B show the system in an initial state in which the system is loaded with fluid-filled syringe 1403 and needle assembly 1405 and ready to perform the injection mechanism. In this state, fluid-filled syringe 1403, needle assembly 1405, flange holder 1423, and plunger retainer 1425 are in a distal position along the central axis. Fluid-filled syringe 1403 contains a volume of fluid that is greater than the amount the amount to be injected. The relative position of plunger retainer 1425 along a central axis at the initial state determines the injection dose and thus the position can be adjusted at this initial state to control injection dose. Needle 1441 is within cover 1443 and actuator ring 1447 is in an initial closed state. Proximal face 1409 is in contact with a skin surface 1449 at a site to receive injection.

Button 1413 is in an initial outward state such that inward protruding struts 1439 maintain spring 1437 in a compressed state, which is in physical connection with flange holder 1423. Inward protruding struts 1439 each contain a protruding portion 1451 that is in contact with flange holder 1423, maintaining the flange holder and plunger retainer 1425 in place and spring 1437 in the compressed state.

Figure 18A:
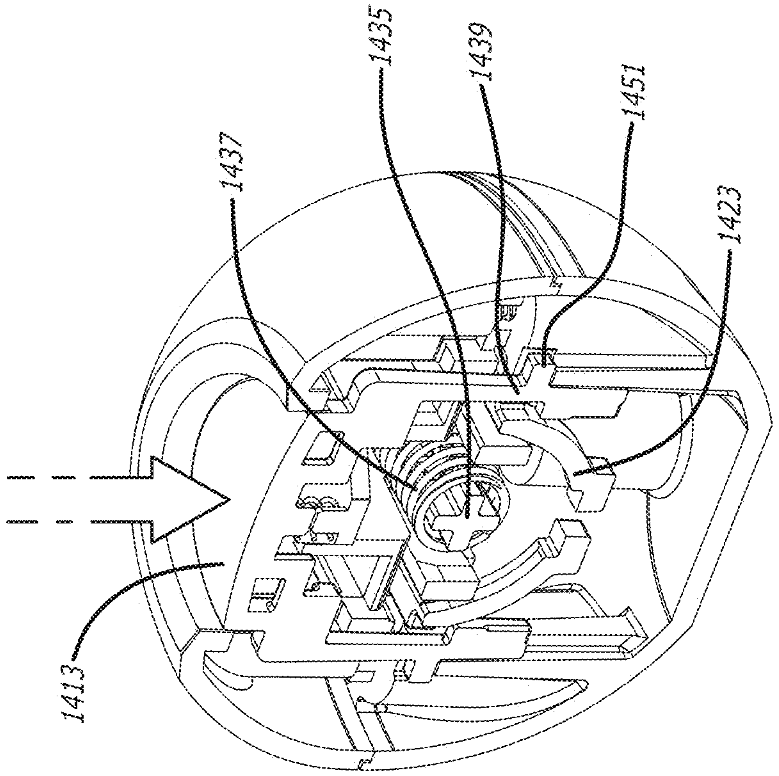
FIGS. 17A to 20 provide illustrations of mechanics of an exemplary ejector system in accordance with various embodiments.
Figure 18B:
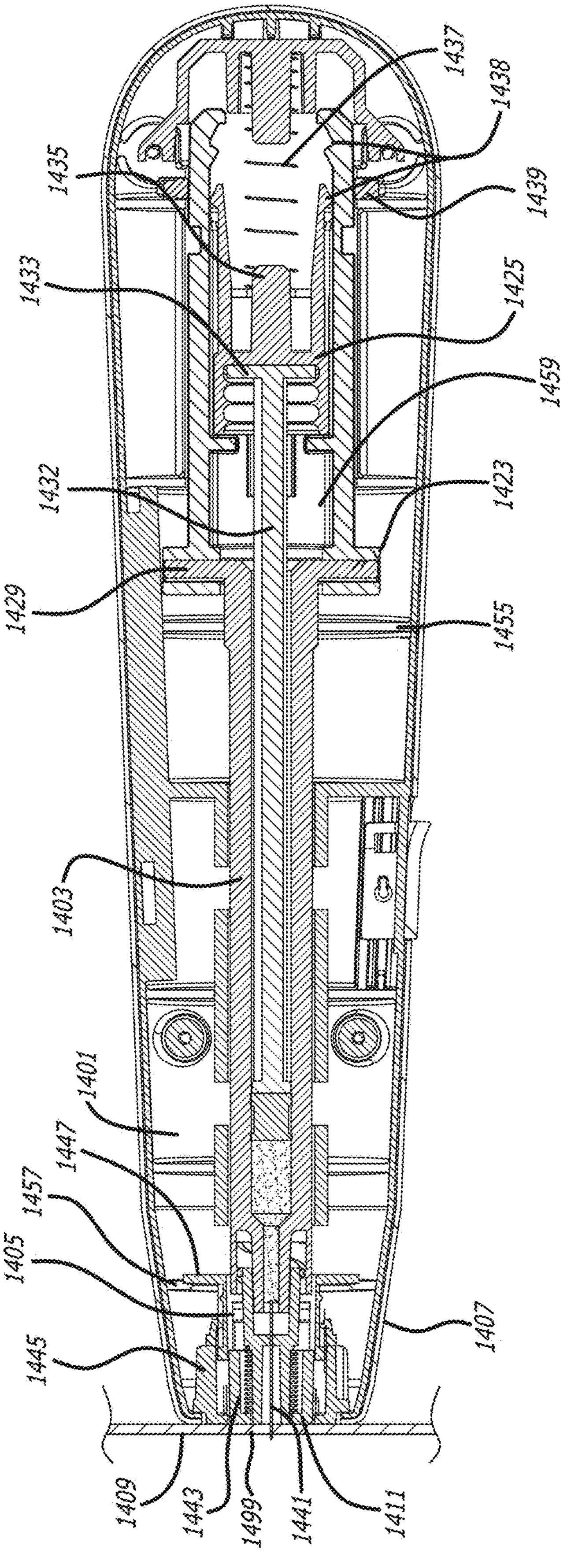

FIGS. 18A and 18B show the initiation of the injection mechanism, resulting in needle 1441 piercing into skin surface 1449. Button 1413 is an actuator of the injection mechanism that when compressed inward 1453 results in the protruding portion 1451 of inward protruding struts 1439 to move further inward such that they are no longer in contact with flange holder 1423. Compressed spring 1437 decompresses moving driver 1435 in a proximal direction along a central axis. Utilizing the spring force, driver 1435 drives flange holder 1423 and plunger retainer 1425 in a proximal direction along a central axis. This results in fluid-filled syringe 1403 and needle assembly 1405 to slide in the proximal direction toward skin surface 1449. As needle assembly 1405 comes into contact with skin surface 1449, cover 1443 contacts the skin and stops its movement, allowing needle 1441 to move proximally past the cover as it pierces into the skin surface. Flange holder 1423 continues to move in the proximal direction until it reaches a flange holder hard stop 1455, halting the proximal movement of the flange holder. The flange holder hard stop also controls the placement of needle assembly 1405 in relationship to skin surface 1449, allowing for precise subdermal or intradermal positioning of the needle tip. Further, as needle assembly 1405 moves in the proximal direction, actuator ring 1447 hits an actuator ring hard stop 1457 opening the actuator ring (i.e., the ring is now held in a more distal position in relation to outer cylinder 1445). By opening the actuator ring, cover 1443 will be allowed to re-cover needle 1441 when the needle is removed from skin surface 1449.

Figure 19:
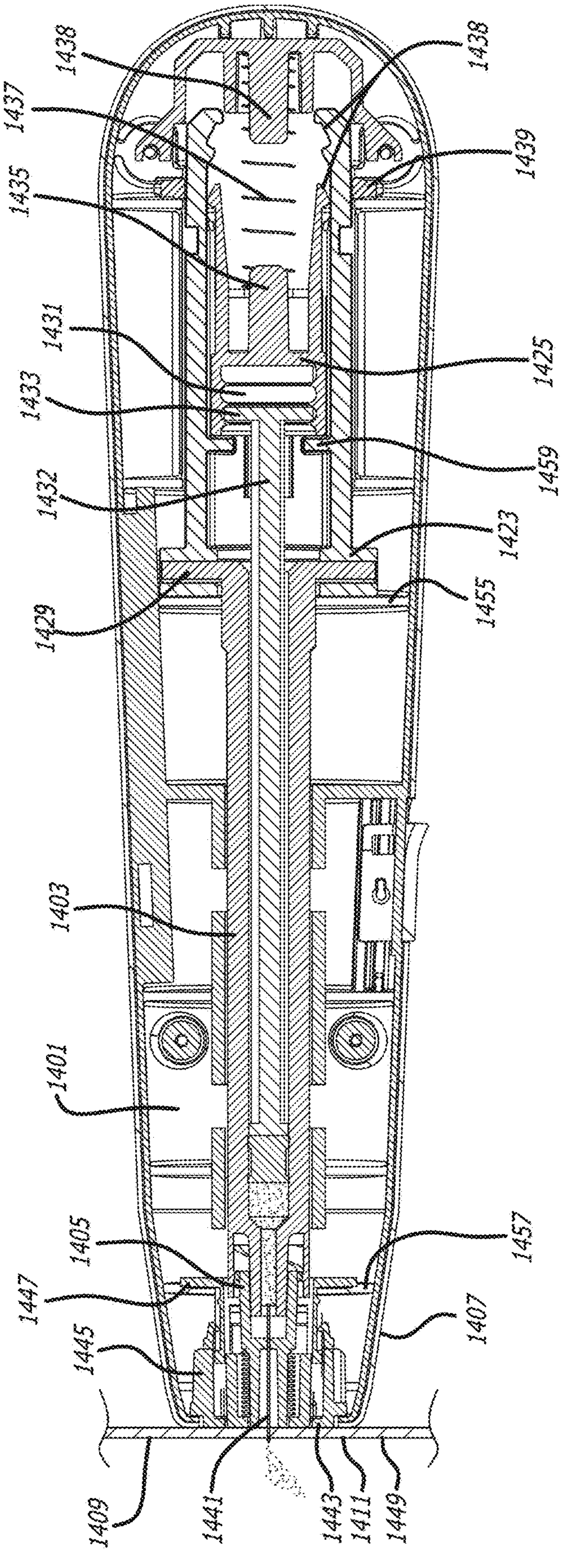

FIG. 19 shows the delivery of a dose of fluid from fluid-filled syringe 1403 through needle 1441 into skin surface 1449. With flange holder 1423 at the flange holder hard stop 1455 position, the flange holder can no longer move in the proximal direction causing latch 1438 to disengage. At this point, driver 1435 continues to drive plunger retainer 1425 in the proximal direction via groove 1434 within flange holder 1423 and slider 1436 of the plunger retainer. As plunger retainer 1425 moves proximally and fluid-filled syringe 1403 remains in place, plunger 1432 is pushed proximally to displace the dose of fluid to be administered, which passes through needle 1441 and into skin surface 1449. Plunger retainer 1425 moves in the proximal direction until it comes into contact with plunger retainer hard stop 1459, which is firmly connected to flange holder 1423. Accordingly, the distance between the position of plunger retainer 1425 and the position of plunger retainer hard stop 1459 controls the fluid dose. When plunger retainer 1425 reaches plunger retainer hard stop 1459, the delivery of fluid into skin 1449 is completed.

Figure 20:
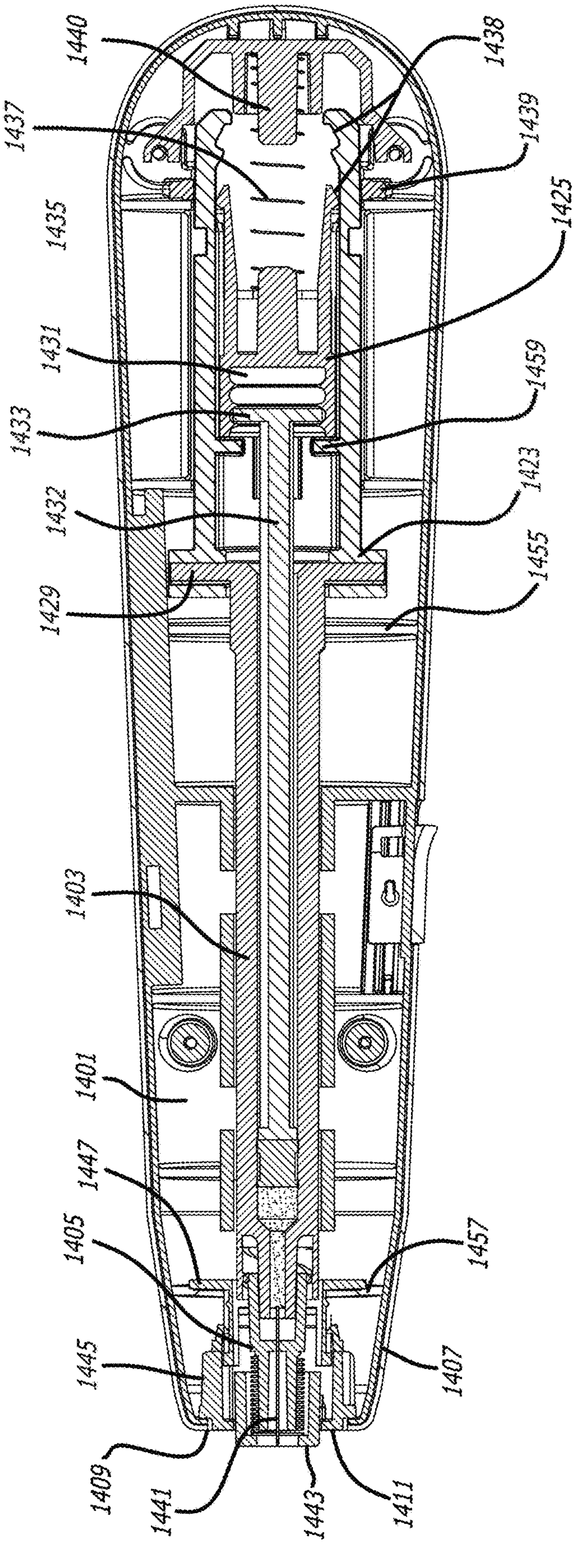

FIG. 20 shows the removal the injector system from skin surface 1449, resulting in cover 1443 covering needle 1441. The fluid-filled syringe 1403, needle assembly 1405, flange holder 1423, and plunger retainer 1425 are in a proximal position. At this time, lid 1415 can be opened up for removal of fluid-filled syringe 1403 and needle assembly 1405. To reset the injector system, plunger retainer 1425 and flange holder 1423 can be slide distally to their initial distal position. Button 1413 can be reset to its outward initial position such that protruding portion 1451 of inward facing struts 1439 hold driver 1435 and compressed spring 1437 in its initial position.

Figure 21:
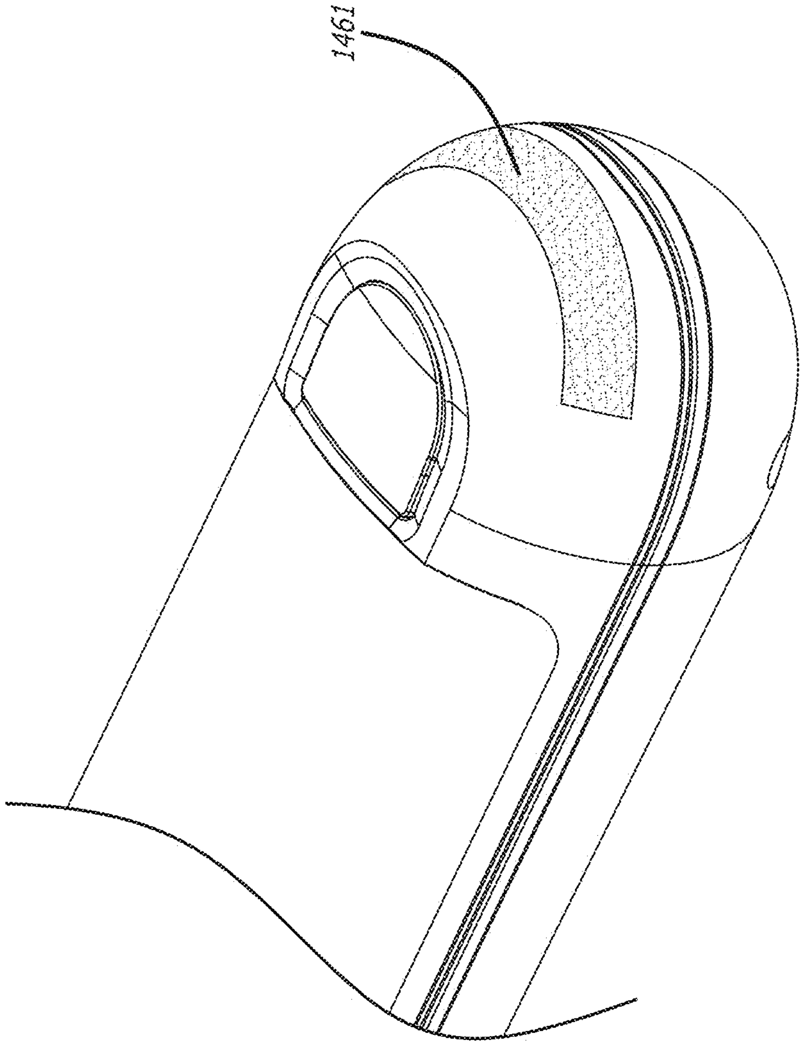
FIGS. 21 to 24 provide illustrations of optional features of an exemplary ejector system in accordance with various embodiments.

FIG. 21 shows the distal end of an injector system having an optional light indicator 1461, which can be battery powered (not shown). Light indicator 1461 can provide various different status indications to help assist a user. Status indications can provide a user notice of operability, readiness of use, warnings, errors, injection status, and battery power status. Various optional status indications that can be utilized include (but are not limited to) on, unloaded, properly loaded, improperly loaded, ready for injection, injection in progress, injection complete, failure to complete injection, and low battery power. The various status indications can be signaled by various light colors and/or patterns of light (e.g., blinking, flashing, wave-like).

Figure 22:
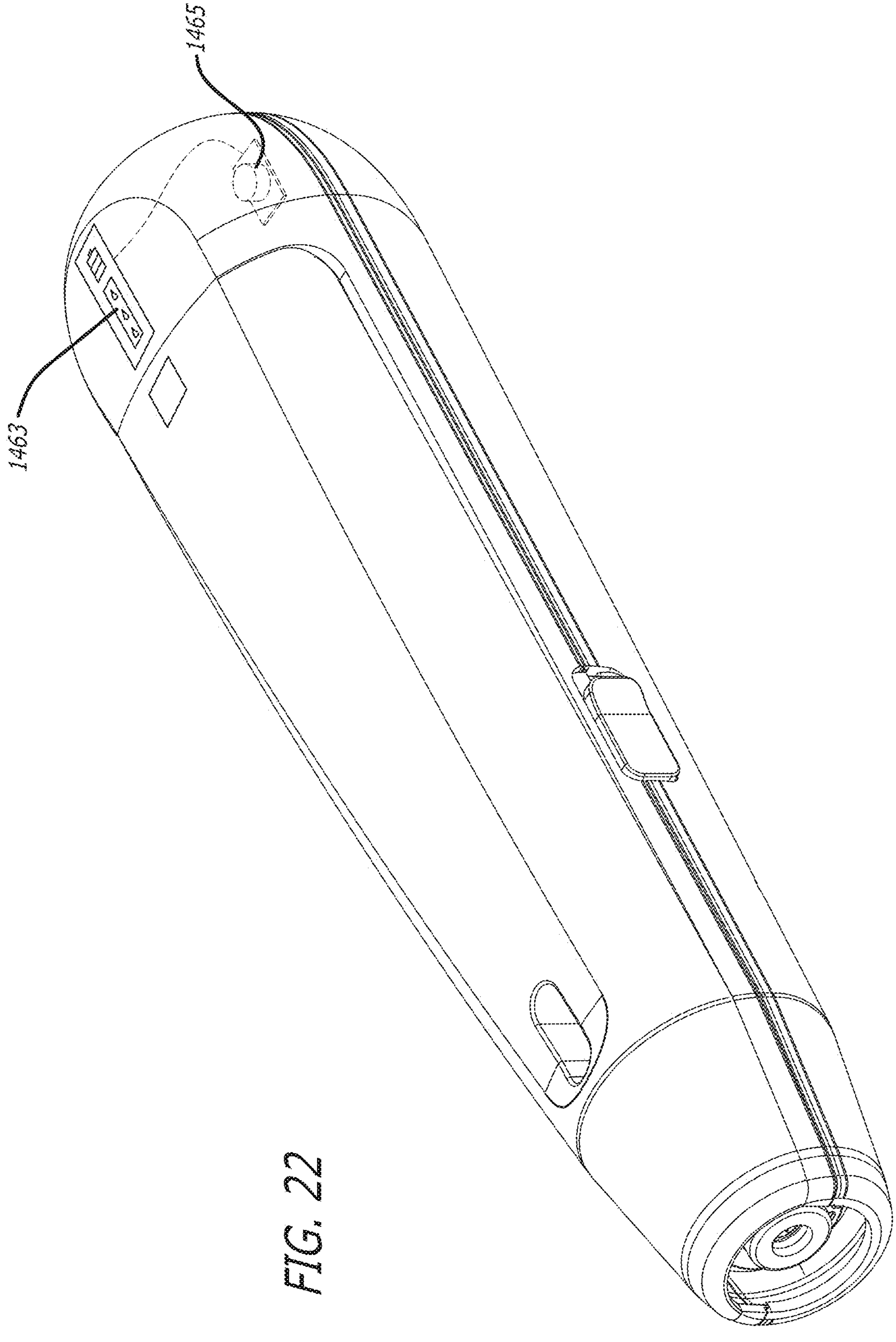

FIG. 22 shows the distal end of an injector system having an optional led screen 1463, which can be powered by a battery 1465. Led screen 1463 can provide various different status indications to help assist a user. Status indications can provide a user notice of operability, readiness of use, warnings, errors, injection status, and battery power status. Various optional status indications that can be utilized include (but are not limited to) on, unloaded, properly loaded, improperly loaded, ready for injection, injection in progress, injection complete, failure to complete injection, and low batter. The various status indications can be signaled by representative icons, color indicators, or script.

Figure 23:
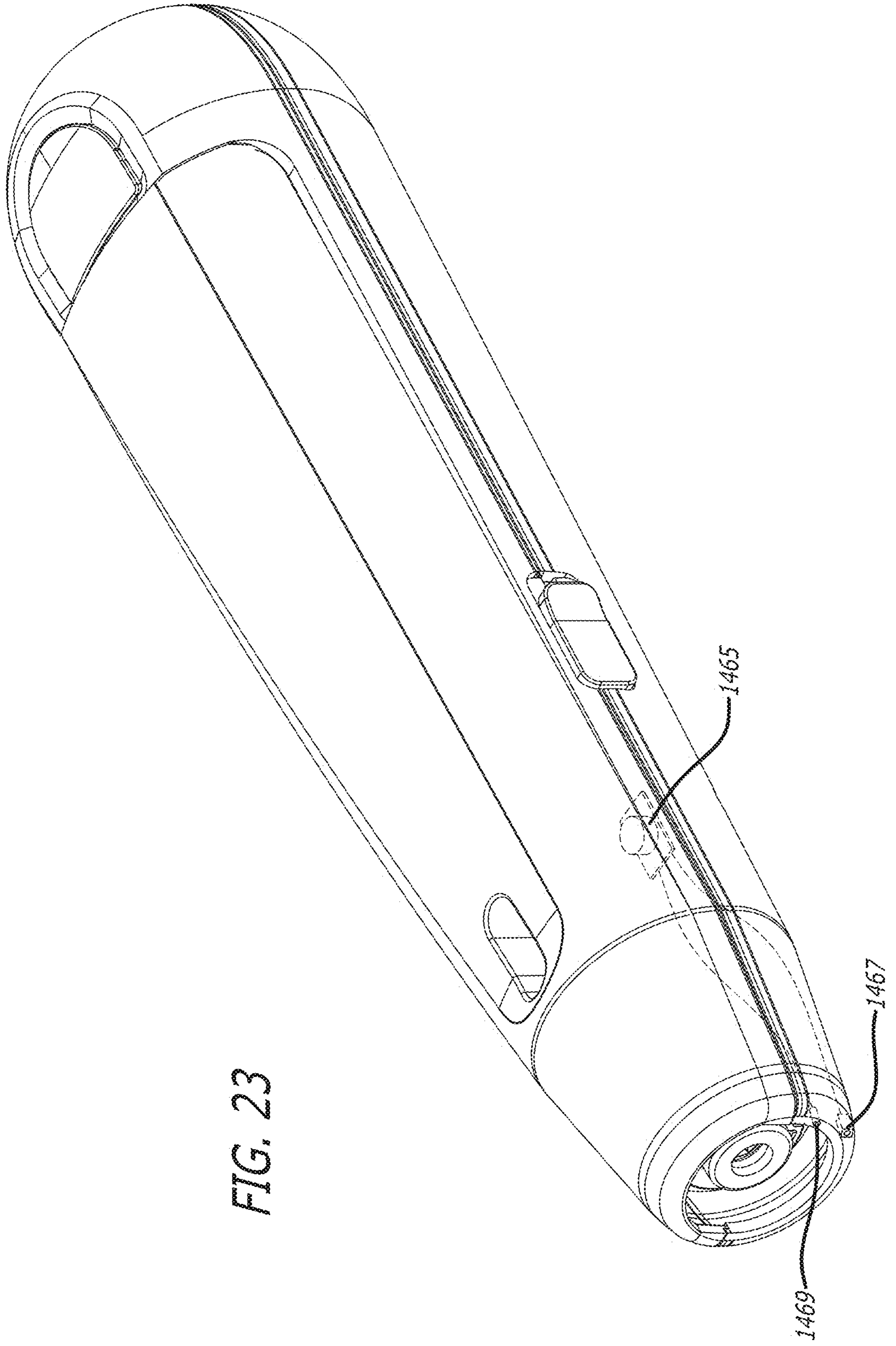

FIG. 23 shows the proximal end of an injector system having an optional camera 1467 and an optional laser light 1469, each of which can be powered by a battery 1465. Camera 1467 can take images of the lesion to be treated. Laser light 1469 can help assist a user to properly locate the injector system onto the lesion to be treated.

Figure 24:
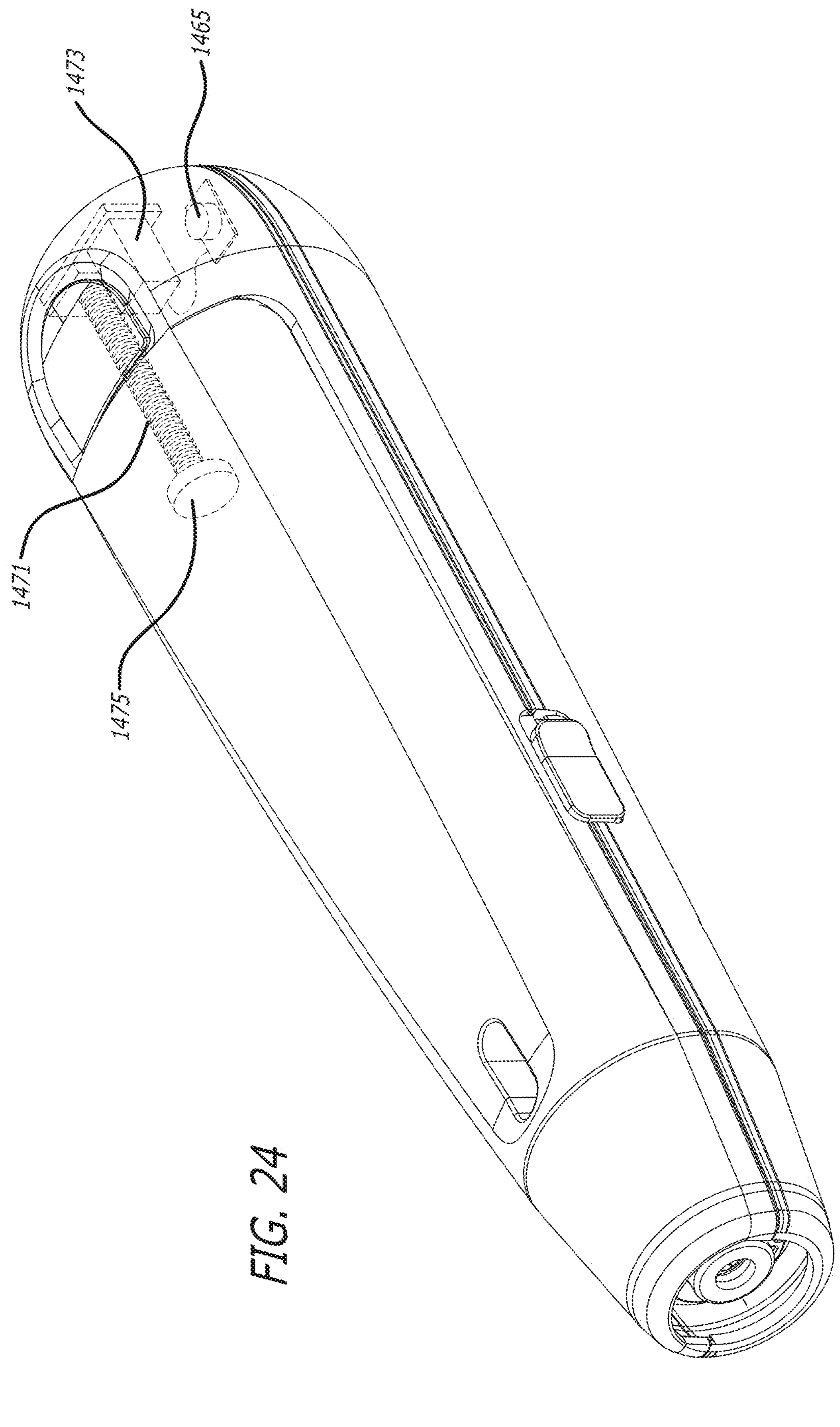
Figure 25:
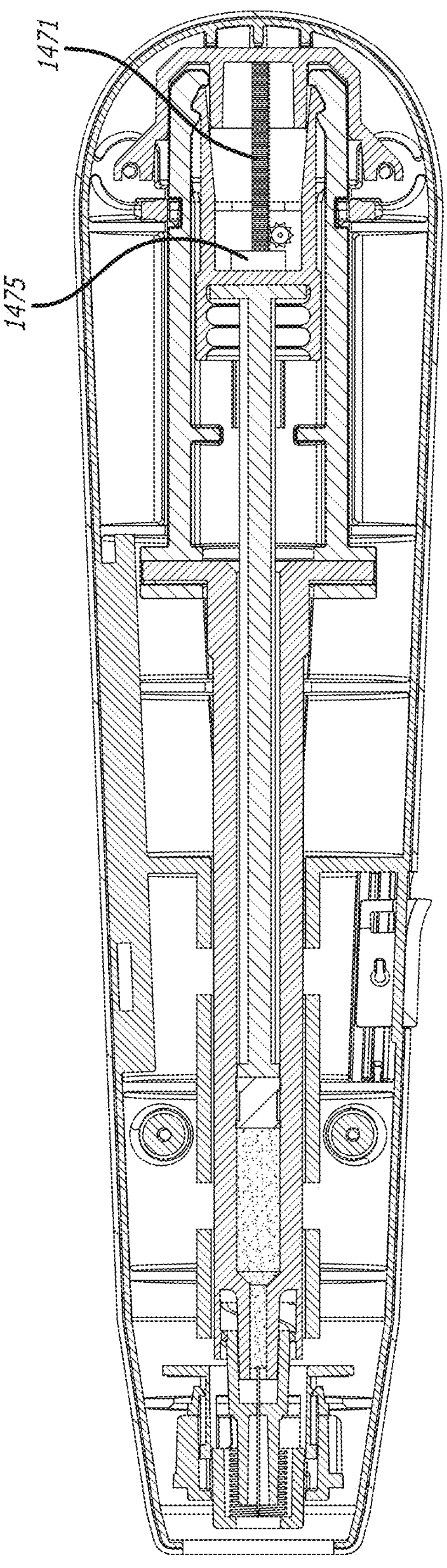

FIGS. 24 and 25 show an electromechanical injector system having an electromechanical linear actuator 1471, a motor 1473 and battery 1465 for powering the motor and linear actuator. Any linear actuator can be utilized, such as (for example) a threaded screw, a worm gear, a rack and pinion, or a solenoid coil. The electromechanical injector shown here can have all the same components and features and have the same mechanistic function of the spring-powered injector system of FIGS. 14 to 20 with the following modifications. Instead of a compressed spring, the electromechanical injector system utilizes a linear actuator 1471 (e.g., as shown a rack and pinion), which can be driven by motor 1473. The linear actuator 1471 includes a head 1475 that is in connection with a driver. Notably, the driver is slightly modified to be compatible with head 1475 instead of a compressed spring. Button 1413 does not hold a spring in a compressed state, but instead initiates the motor to turn the pinion, causing head 1475 and the driver to move in the proximal direction. The movement of the driver in the proximal direction can proceed to drive the injection mechanism as shown in FIGS. 18A to 20 and described in accompanying text. The linear actuator 1471 can also perform the reset (i.e., pull driver in distal direction), instead of manually resetting the injector system.

FIGS. 26 to 29 depict an exemplary needle assembly and mechanism for ensuring the needle remains covered before and after fluid injection. The needle assembly depicted here can be utilized with any syringe, with or without an injector system. In some implementations, the needle assembly depicted here is utilized with the injector system shown in FIGS. 14 to 20.

Figure 26A:
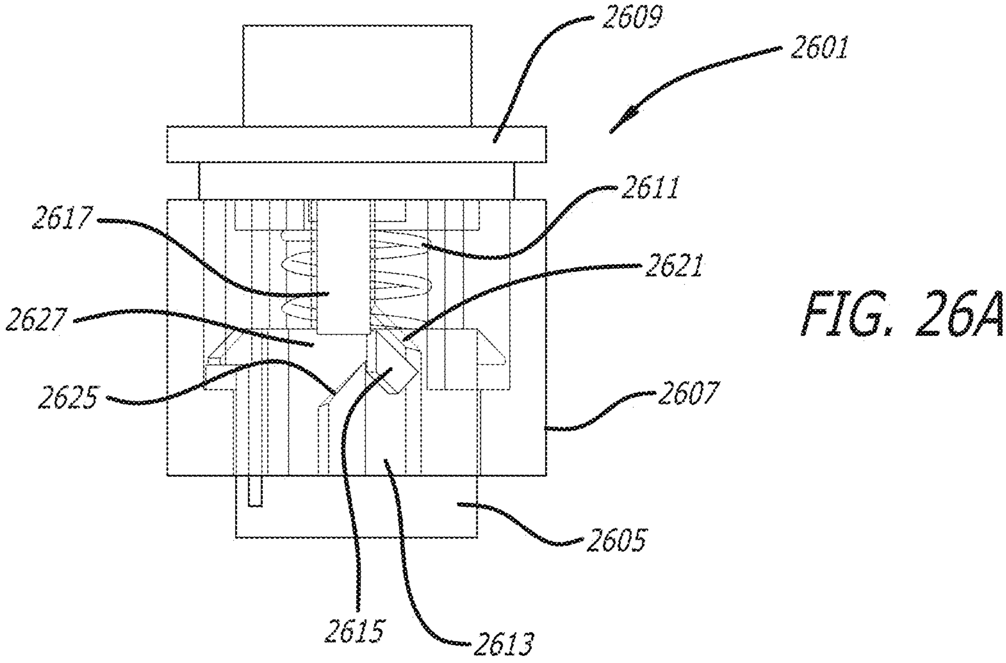
FIGS. 26 to 29 provide illustrations of a needle assembly in accordance with various embodiments.
Figure 26B:
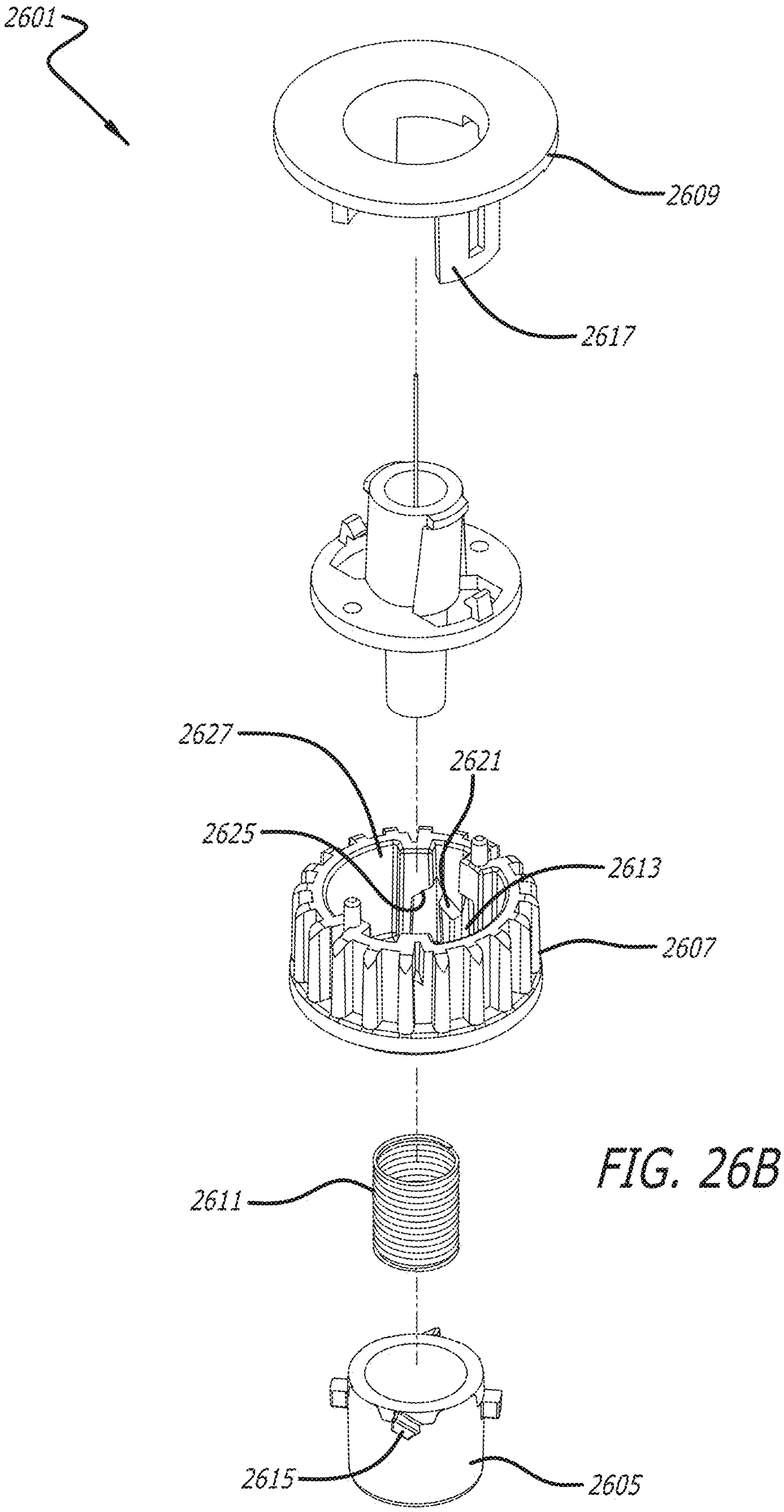

FIG. 26 provides needle assembly 2601 in an initial state. Needle assembly 2601 comprises a needle 2603, a needle cover 2605, an outer cylinder 2607, an actuator ring 2609, and a spring 2611. Note, the outer cylinder is portrayed as transparent to assist in understanding the mechanism of the needle assembly. In the initial state, spring 2611 is decompressed and in connection with needle cover 2605 such that pushing the cover inward compresses spring 2611. In the decompressed stated, spring 2611 ensures that needle cover 2605 extends beyond the tip of needle 2603 such that the tip is not exposed, preventing any harm to a user. Actuator ring 2609 is initially provided as closed, with the ring being in a proximal position relative to outer cylinder 2607.

The inner face of outer cylinder 2607 has a topography that includes a slotted track 2613 that cooperatively interacts with a protruding slider 2615 that extends from the outer face of cover 2605. In combination with spring 2611, slotted track 2613 and protruding slider 2615 works with an actuator arm 2617 that extends inwardly from actuator ring 2609 to ensure that needle 2603 remains within cover 2605 prior to injection.

Figure 27:
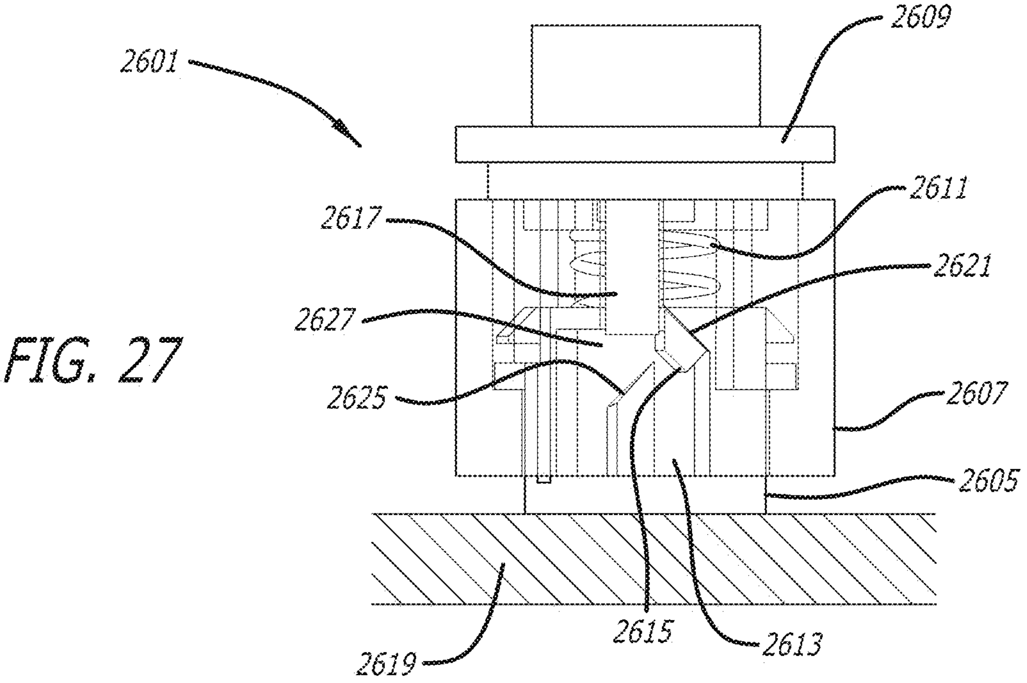

FIG. 27 shows needle assembly 2601 pushed against a skin surface 2619. Needle cover 2605 is pushed inwardly but maintains coverage of needle 2603 while actuator ring 2609 remains closed. Actuator arm 2617 extends into slotted track 2613 to prevent protruding slider 2615 from sliding further inwardly, providing a hard stop of further inward movement of needle cover 2605 such that the needle tip remains unexposed.

Figure 28:
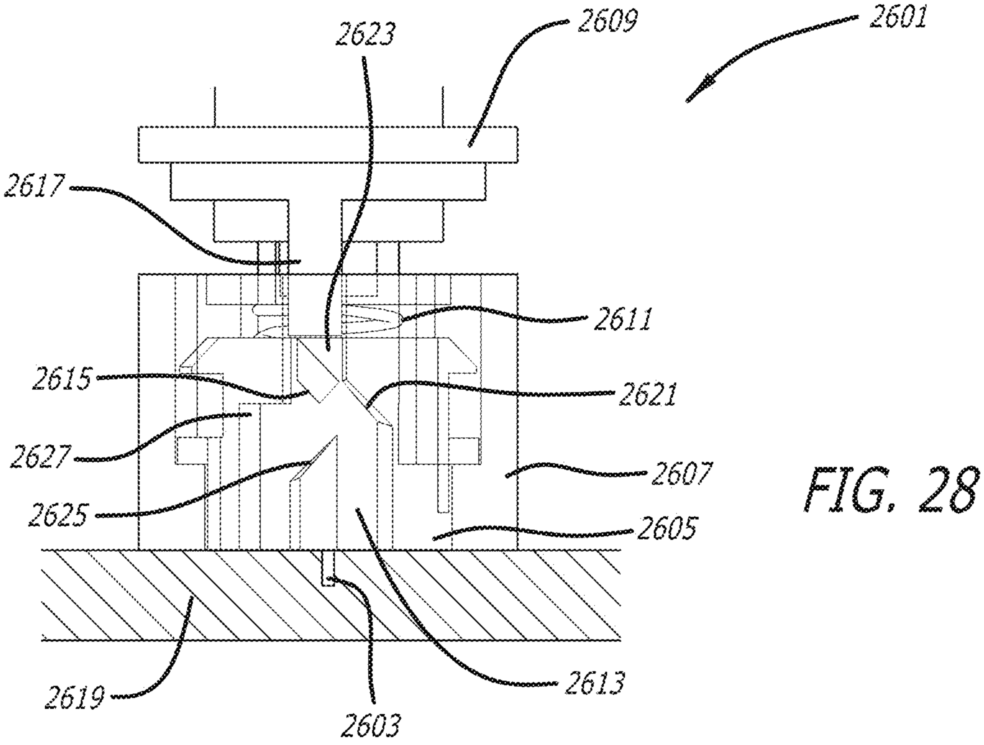

FIG. 28 shows actuator ring 2609 opened by pulling the ring distally away from outer cylinder 2607, resulting in removal of actuator arm 2617 from slotted track 2613. With actuator arm 2617 removed, protruding slider 2615 can move inwardly along slotted track 2613, allowing needle cover 2605 to move further inward and exposing the tip of needle 2603. Needle 2603 can insert into skin surface 2619, such that a fluid can be intradermally or subdermally injected via a syringe in operable connection with needle assembly 2601.

Slotted track 2613 can include an angled wall 2621 that causes protruding slider 2615 to move along the inner circumference of outer cylinder 2607 as the slider is pushed inwardly, resulting in needle cover 2605 to rotate about a central axis. Rotation of protruding slider 2615 allows it to enter within a slotted track 2623 that is opened up by the outward movement of actuator arm 2617. Protruding slider 2615 can move inwardly within slotted track 2623, reaching a hard stop when it comes into contact with actuator arm 2617. When protruding slider 2615 reaches actuator arm 2617, needle cover 2605 cannot move further inward and provides a limited exposure of needle 2603. Accordingly, the position of actuator arm 2617 when actuator ring 2609 is opened provides a limited depth that the needle can insert within skin surface 2619, controlling the depth point of fluid injection.

Figure 29:
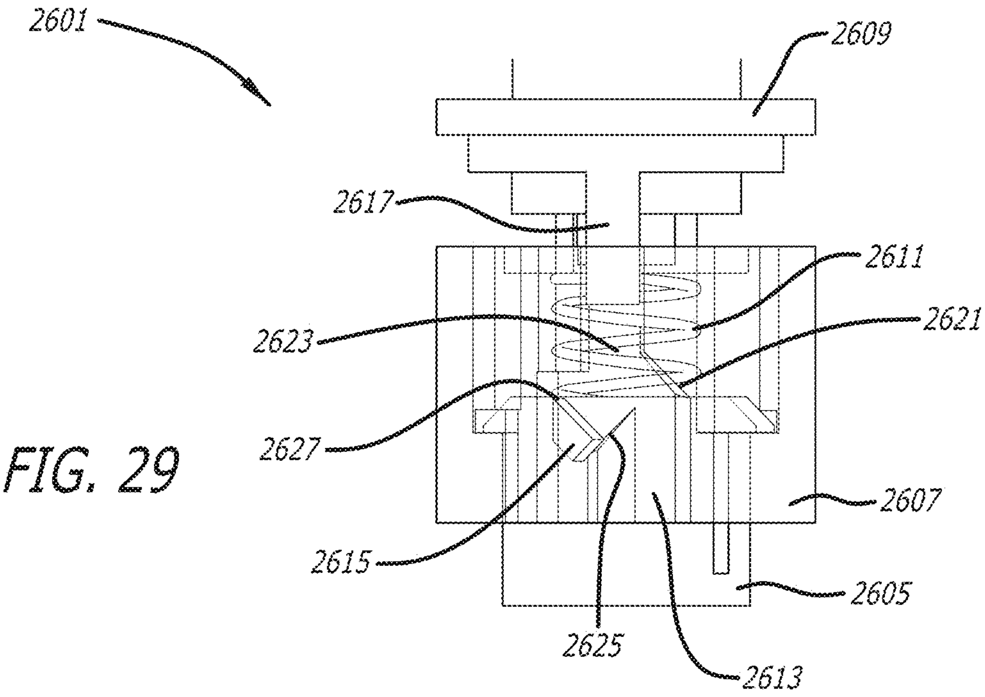

FIG. 29 shows removal of needle assembly 2601 from skin surface 2619. Notably, when needle cover 2605 is pushed inward, spring 2611 is compressed. And thus removal of needle assembly 2601 from skin surface 2619 results in spring 2611 pushing needle cover 2605 outwardly and extends beyond the tip of needle 2603. As needle cover 2605 is pushed outward, protruding slider 2615 slides outwardly through slotted track 2623 until it comes in contact with angled wall 2625. The force provided by the compression of spring 2611 in conjunction with angled wall 2625 causes protruding slider 2615 to rotate along the inner circumference of outer cylinder 2607 as the slider is pushed outwardly, resulting in needle cover 2605 to rotate about a central axis. Rotation of protruding slider 2615 allows it to come into contact with a hard corner 2627, resulting in the slider situating between the hard corner and angled wall 2625. To lock protruding slider 2615 within hard corner 2627, actuator ring 2609 can be reclosed, resulting in actuator arm 2617 refilling slotted track 2623, preventing the slider from rotating back along the inner circumference of outer cylinder 2607. Reclosing of actuator ring 2609 can optionally be secured via a latch or other securing mechanism such that the actuator ring cannot be reopened, preventing re-exposure of needle 2603.

Figure 30A:
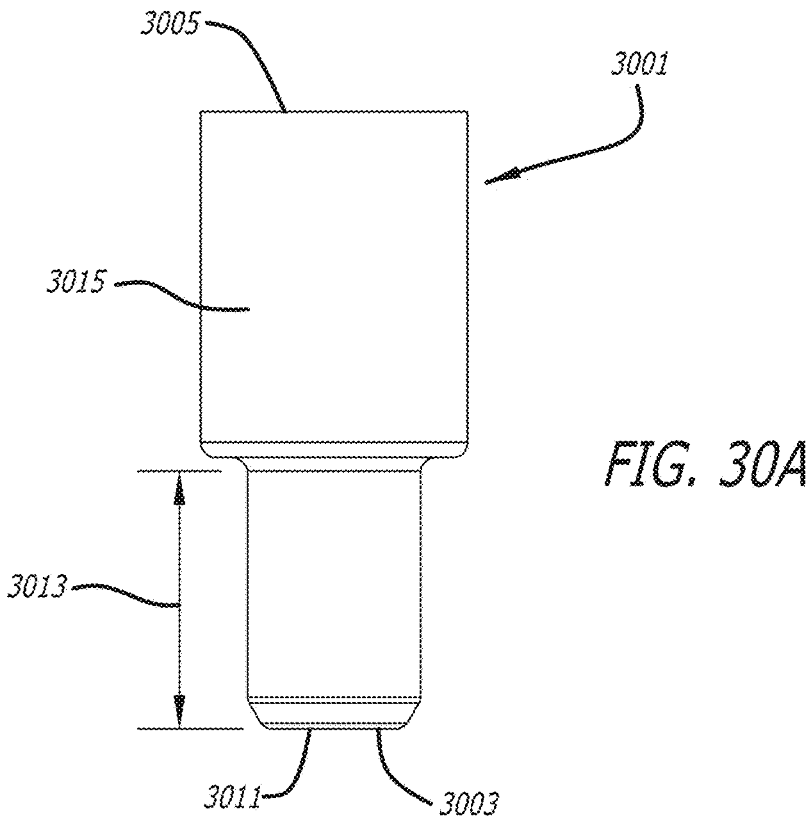
FIGS. 30A and 30B provide illustrations of a needle cap in accordance with various embodiments.
Figure 30B:
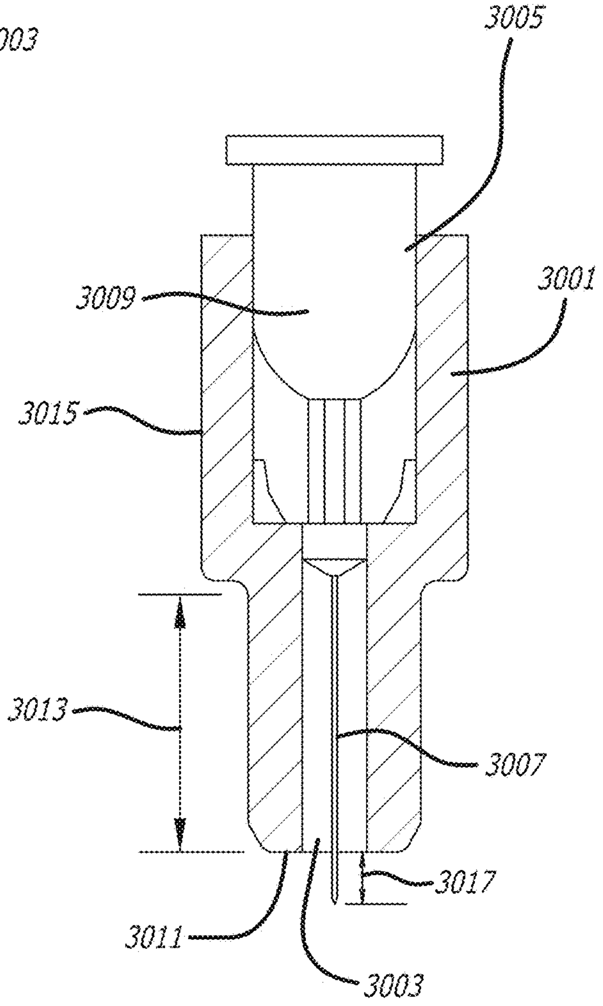

Provided in FIGS. 30A and 30B is an exemplary needle cap for controlling depth needle penetration within the site of injection. Needle cap 3001 contains a proximal orifice 3003 and distal orifice 3005. Needle cap 3001 can fit upon a needle 3007 with distal orifice 3005 situated and fitted onto a needle base 3009. Accordingly, distal orifice 3005 can have a circumference that snugly fits around needle base 3009 such that it can securely hug the base. Needle 3007 can extend through proximal orifice 3003 such that the tip of the needle is a particular distance from the orifice and proximal face 3011. This particular distance can used to define a particular depth for fluidic injection. Accordingly, various implementations of needle caps have a length 3013 from needle cap base 3015 to proximal face 3011 that corresponds to a needle length and an injection depth such that the portion of needle exposed beyond the proximal face 3017 is the injection depth.

Various methods can be performed for injecting fluid at a particular depth utilizing a needle and needle cap. One exemplary method can be as follows:

provide a fluid-filled syringe in operable connection with a needle;

place a needle cap over needle such that a cap base fits onto a needle base and the needle tip extends beyond a proximal orifice at a particular distance, the particular distance defining an injection depth;

insert the needle into an injection site such that the proximal face of the cap is in contact with the surface of the injection site, resulting in the needle tip at the injection depth within the injection site;

injecting the fluid from the fluid-filled syringe at the injection depth via the fluid-filled syringe and needle.

Applications of Fluid Delivery

The various embodiments of intradermal or subdermal fluid delivery systems can be utilized in a number of applications that require liquid delivery into the skin. In certain embodiments, a fluid delivery system is used for delivery of medication or supplement into the skin. In certain embodiments, triamcinolone (Kenalog) is utilized within a fluid delivery system. In certain embodiments, hyaluronic acid is utilized within a fluid delivery system. In certain embodiments, collagen or a collagen stimulating agent is utilized within a fluid delivery system.

Triamcinolone is a glucocorticoid use to treat various skin ailments, including (but not limited to) acne, eczema, dermatitis, allergies, and rash. Triamcinolone can reduce swelling, itching, and redness.

Treatment of an acne lesion can reduce the swelling and redness within 12 hours with single dose at a volume of 0.01 mLs to 0.20 mLs and at a concentration between 1 mg/mL and 10 mg/mL. Accordingly, a solution containing triamcinolone can be contained within fluid-containing portion of a cartridge or syringe, as described herein. The triamcinolone-containing cartridge or syringe can be utilized within an injector system. A needle or microneedle can penetrate the skin the requisite amount for intralesion delivery (e.g., intradermal or subdermal delivery at the site of the lesion). The injector system can inject the triamcinolone into the lesion as a treatment. The treatment can be performed multiple times on a single lesion or can be performed on multiple lesions, as needed. In many instances, a single dose will result in substantial clearance of an acne lesion. Similar procedures can be performed on other skin ailments.

Hyaluronic acid is a glycogen that is naturally produced in the skin. Hyaluronic acid injections into the skin can boos the amount of localized skin hyaluronic acid. Benefits of hyaluronic acid include (but are not limited to) mitigating the appearance of aging of skin, reducing wrinkles, reducing inflammation in the skin, and assisting in would healing.

Collagen is protein that is naturally produced in the skin. Collagen injections (or injection of collagen stimulating agents) into the skin can boost the amount of localized skin collagen. Benefits of collagen (or collagen stimulating agent) include (but are not limited to) reducing appearance of scars (especially acne scars), flattening out wrinkles, and filling-in skin depression. Collagen stimulating agents include (but are not limited to) microneedling, vitamin C, proline, glycine, copper, aloe vera, *ginseng*, and algae.

Various medications and supplements can be combined within the same cartridge for use in intradermal or subdermal fluid delivery system. For instance, one exemplary combination is triamcinolone with collagen (or a collagen stimulating agent).

What is claimed is:

1. A system for intradermal or subdermal fluid delivery into a site of injection, comprising:

a housing compartment comprising a flange holder system, a plunger retainer system, and an actuator of an injection mechanism that expels a controlled dose fluid, wherein the flange holder system comprises a movable flange holder and a flange holder hard stop and the plunger retainer system comprises a moveable plunger retainer and a plunger retainer hard stop, and wherein the flange holder and the plunger retainer are each movable in a proximal direction along a central axis of the housing compartment;

a fluid-filled syringe comprising a flange and a plunger, wherein the flange is situated within the flange holder and plunger is situated in the plunger retainer; and a needle assembly attached to the fluid-filled syringe, the needle assembly comprising a needle that is in operable connection with the fluid-filled syringe;

wherein actuation of the injection mechanism via the actuator results in the flange holder and the plunger retainer moving in the proximal direction resulting in moving the fluid-filled syringe inclusive of the flange and the plunger, and the needle assembly in the proximal direction until the flange holder contacts the flange holder hard stop halting the proximal movement of the flange and the needle assembly;

wherein when the flange holder contacts the flange holder hard stop, the plunger retainer continues to move in the proximal direction resulting in the plunger to continue to move in the proximal direction until the plunger retainer contacts the plunger retainer hard stop halting the proximal movement of the plunger; and wherein the continued proximal movement of the plunger after the halting of the proximal movement of the flange and the needle assembly results in expulsion of the controlled dose of fluid from the fluid-filled syringe via the needle of the needle assembly.

2. The system of claim 1, wherein the flange holder comprises a groove, and the plunger retainer comprises a slider that cooperates within the groove; and wherein when the flange holder contacts the flange holder hard stop, the plunger retainer continues to move in the proximal direction via the slider within the groove.

3. The system of claim 1, wherein a latch connects the flange holder and the plunger retainer; and wherein when the flange holder contacts the flange holder hard stop, the latch is released allowing the plunger retainer to continue to move in the proximal direction independent of the flange holder movement.

4. The system of claim 3, further comprising a force for providing proximal movement, wherein the plunger retainer is in connection with the force for providing proximal movement such that the plunger retainer moves in the proximal direction via the actuation of the injection mechanism; and wherein the flange holder moves in the proximal direction via the latch connecting the flange holder and the plunger retainer.

5. The system of claim 4, wherein the force for providing proximal movement is a compressed spring.

6. The system of claim 4, wherein the force for providing proximal movement is an electromechanical linear actuator.

7. The system of claim 1, wherein the dose amount of the controlled dose of fluid is determined in part by the continued proximal movement of the plunger after the halting of the proximal movement of the flange and the needle assembly.

8. The system of claim 1, wherein the flange holder contains an indentation that is contoured to the shape of the flange.

9. The system of claim 1, wherein the flange holder contains an indentation that is contoured to the shape of the flange.

10. The system of claim 1, wherein the plunger retainer contains at least one indentation that is contoured to the shape of a plunger grip at the distal end of the plunger.

11. The system of claim 10, wherein the plunger retainer contains a plurality of indentations that allow for flexibility of the plunger grip location.

12. The system of claim 1, wherein the actuator of the injection mechanism comprises a button, wherein one or more inward protruding struts is in connection with button and the flange holder; wherein when the button is depressed, the one or more inward protruding struts prevents proximal movement of the flange holder; and wherein compression of the button results in a disconnection between the one or more inward protruding struts and the flange holder, allowing proximal movement of the flange holder.

13. The system of claim 1, wherein compression of the button results in linear force provided by an electromechanical linear actuator to provide proximal movement of the plunger retainer.

14. The system of claim 1, wherein the needle has a length that such that the needle tip extends beyond the proximal face a length equal to an intradermal insertion depth when inserted into skin of an individual.

15. The system of claim 1, wherein the needle assembly further comprises a needle cap; and wherein the needle has a length such that the needle tip extends beyond the needle cap a length equal to an intradermal insertion depth when inserted into skin of an individual.

16. The system of claim 1, wherein the needle assembly further comprises a needle cover that surrounds the needle and a spring in connection with the needle cover; wherein when the spring is decompressed, the needle cover prevents exposure of a tip of the needle; and wherein when the spring is compressed, the tip of the needle is exposed.

17. A housing compartment for receiving a fluid filled syringe and a needle assembly to form a system for intradermal or subdermal fluid delivery into a site injection, the housing compartment comprising:

a flange holder system, a plunger retainer system, and an actuator of an injection mechanism that expels a controlled dose fluid, wherein the flange holder system comprises a movable flange holder and a flange holder hard stop and the plunger retainer system comprises a moveable plunger retainer and a plunger retainer hard stop, wherein the flange holder and the plunger retainer are each movable in a proximal direction along a central axis of the housing compartment, and wherein the flange holder and the plunger retainer are connected by a latch;

wherein actuation of the injection mechanism via the actuator results in the flange holder and the plunger retainer moving in the proximal direction until the flange holder contacts the flange holder hard stop halting the proximal movement of the flange holder; and wherein when the flange holder contacts the flange holder hard stop, the latch is released allowing the plunger retainer to continue to move in the proximal direction independent of the flange holder movement; and wherein upon release of the latch, the plunger retainer continues to move in the proximal direction until the plunger retainer contacts the plunger retainer hard stop halting the proximal movement of the plunger retainer.

18. The housing compartment of claim 17, wherein the flange holder comprises a groove, and the plunger retainer comprises a slider that cooperates within the groove; and wherein when the flange holder contacts the flange holder hard stop, the plunger retainer continues to move in the proximal direction via the slider within the groove.

19. The housing compartment of claim 17, further comprising a force for providing proximal movement, wherein the plunger retainer is in connection with the force for providing proximal movement such that the plunger retainer moves in the proximal direction via the actuation of the injection mechanism; and wherein the flange holder moves in the proximal direction via the latch connecting the flange holder and the plunger retainer.

20. The housing compartment of claim 19, wherein the force for providing proximal movement is a compressed spring.

21. The housing compartment of claim 19, wherein the force for providing proximal movement is an electromechanical linear actuator.

22. The system of claim 17, wherein the flange holder contains an indentation that is contoured to a shape of a flange of a syringe.

23. The housing compartment of claim 17, wherein the plunger retainer contains at least one indentation that is contoured to the shape of a plunger grip at the distal end of a plunger of a syringe.

24. The housing compartment of claim 23, wherein the plunger retainer contains a plurality of indentations that allow for flexibility of the plunger grip location.

25. The housing compartment of claim 17, wherein the actuator of the injection mechanism comprises a button, wherein one or more inward protruding struts is in connection with button and the flange holder; wherein when the button is depressed, the one or more inward protruding struts prevents proximal movement of the flange holder; and wherein compression of the button results in a disconnection between the one or more inward protruding struts and the flange holder, allowing proximal movement of the flange holder.

26. The housing compartment of claim 17, wherein the actuator of the injection mechanism comprises a button, wherein compression of the button results in linear force provided by an electromechanical linear actuator to provide proximal movement of the plunger retainer.

27. A method for injecting a particular dose of fluid at a particular depth, the method comprising:

providing an injector system comprising:

a housing compartment comprising a flange holder system, a plunger retainer system, and an actuator of an injection mechanism that expels a controlled dose fluid, wherein the flange holder system comprises a movable flange holder and a flange holder hard stop and the plunger retainer system comprises a moveable plunger retainer and a plunger retainer hard stop, and wherein the flange holder and the plunger retainer are each movable in a proximal direction along a central axis of the housing compartment;

a fluid-filled syringe comprising a flange and a plunger, wherein the flange is situated within the flange holder and plunger is situated in the plunger retainer; and a needle assembly attached to the fluid-filled syringe, the needle assembly comprising a needle that is in operable connection with the fluid-filled syringe;

placing the needle assembly proximal to a site of injection; and actuating the actuator, wherein actuation the actuator results in the flange holder and the plunger retainer moving in the proximal direction resulting in moving the fluid-filled syringe inclusive of the flange and the plunger, and the needle assembly in the proximal direction until the flange holder contacts the flange holder hard stop halting the proximal movement of the flange and the needle assembly, wherein movement of the flange holder in the proximal direction results in the needle of the needle assembly inserting into the site of injection at a particular depth;

wherein when the flange holder contacts the flange holder hard stop, the plunger retainer continues to move in the proximal direction resulting in the plunger to continue to move in the proximal direction until the plunger retainer contacts the plunger retainer hard stop halting the proximal movement of the plunger; and wherein the continued proximal movement of the plunger after the halting of the proximal movement of the flange and the needle assembly results in the expulsion of a controlled dose of fluid from the fluid-filled syringe via the needle of the needle assembly.

28. The method of claim 27, wherein the site of injection is skin of an individual.

29. The method of claim 28, wherein the site of injection is a skin lesion.

30. The method of claim 27, wherein the controlled dose expelled is approximately 0.01 cc to 1 cc.

31. The method of claim 27, wherein the particular depth that the needle inserts into the site of injection is approximately between 0.5 mm to 2.0 mm.

32. The method of claim 27, wherein the expelled fluid is a medication or supplement for the skin.

33. The method of claim 27, wherein the expelled fluid is triamcinolone, hyaluronic acid, collagen, or a collagen stimulating agent.

* * * * *